(12) United States Patent
Koshio et al.

(10) Patent No.: US 7,807,664 B2
(45) Date of Patent: Oct. 5, 2010

(54) 4,4-DIFLUORO-1,2,3,4-TETRAHYDRO-5H-1-BENZAZEPINE DERIVATIVE OR SALT THEREOF

(75) Inventors: Hiroyuki Koshio, Tokyo (JP); Issei Tsukamoto, Tokyo (JP); Akio Kakefuda, Tokyo (JP); Seijiro Akamatsu, Tokyo (JP); Chikashi Saitoh, Tokyo (JP)

(73) Assignee: Astella Pharma Inc., Tokyo (JP)

( * ) Notice: Subject to any disclaimer, the term of this patent is extended or adjusted under 35 U.S.C. 154(b) by 793 days.

(21) Appl. No.: 11/598,732

(22) Filed: Nov. 14, 2006

(65) Prior Publication Data

US 2007/0167429 A1      Jul. 19, 2007

Related U.S. Application Data

(63) Continuation of application No. 10/554,150, filed as application No. PCT/JP2004/005998 on Apr. 26, 2004, now Pat. No. 7,183,271.

(30) Foreign Application Priority Data

Apr. 28, 2003 (JP) ............................. 2003-123032
Dec. 1, 2003 (JP) ............................. 2003-401126

(51) Int. Cl.
*A61P 7/12*    (2006.01)
*A61K 31/55*   (2006.01)
*C07D 223/16*  (2006.01)

(52) U.S. Cl. ................................ 514/213.01; 540/593
(58) Field of Classification Search ............ 514/213.01; 540/593
See application file for complete search history.

(56) References Cited

U.S. PATENT DOCUMENTS

| | | | |
|---|---|---|---|
| 5,710,150 | A | 1/1998 | Taniguchi et al. |
| 6,096,735 | A | 8/2000 | Ogawa et al. |
| 6,096,736 | A | 8/2000 | Ogawa et al. |
| 6,335,327 | B1 | 1/2002 | Ogawa et al. |
| 6,340,678 | B1 | 1/2002 | Matsuhisa et al. |
| 6,547,395 | B1 | 4/2003 | Neal et al. |
| 6,642,223 | B2 | 11/2003 | Ogawa et al. |
| 7,183,271 | B2 | 2/2007 | Koshio et al. |
| 2002/0049194 | A1 | 4/2002 | Ogawa et al. |
| 2003/0087892 | A1 | 5/2003 | Ashworth et al. |

FOREIGN PATENT DOCUMENTS

| | | |
|---|---|---|
| EP | 0716083 A1 | 6/1996 |
| EP | 0987264 A1 | 3/2000 |
| EP | 1445253 A1 | 8/2004 |
| JP | 8-301848 | 11/1996 |
| JP | 9-221475 | 8/1997 |
| JP | 9-221476 | 8/1997 |
| JP | 2926335 | 5/1999 |
| JP | 11-349570 | 12/1999 |
| JP | 2000-351768 | 12/2000 |
| JP | 3215910 | 8/2001 |
| RU | 2 137 760 C1 | 9/1999 |
| WO | WO-95/06035 | 3/1995 |
| WO | WO 95/34540 | 12/1995 |
| WO | WO-97/22591 | 6/1997 |
| WO | WO-98/39325 | 9/1998 |
| WO | WO-99/06403 | 2/1999 |
| WO | WO-99/06409 | 2/1999 |
| WO | WO-00/46224 | 8/2000 |
| WO | WO-01/49682 A1 | 7/2001 |
| WO | WO 03/042181 A1 | 5/2003 |

OTHER PUBLICATIONS

Del Tredici et al., Identification of Novel Selective V.sub.2 Receptor Non-Peptide Agonists, Biochemical Pharmacology, vol. 76, pp. 1134-1141, 2008.*
European Search Report received Jun. 25, 2008, in corresponding application EP 04 72 9502.
Office Action received Aug. 31, 2007, in related application 2005136863.
Ogawa et al.; "Pharmaceutical Composition"; Patent Abstracts of Japan of JP 11-060488, Mar. 2, 1999.
Kondo et al., "Novel Design of Nonpeptide AVP V2 Receptor Agonists: Structural Requirements for and Agonist Having 1-(4-Aminobenzoyl)-2,3,4,5-tetrahydro-1H-1-benzazepine as a Template," J. med. Chem. (Nov. 2000) vol. 43, No. 23, pp. 4388-4397.
Canadian Office Action (2 pages) mailed Nov. 2, 2009, in corresponding application No. 2,521,492.
European Office Action (5 pages) mailed Feb. 23, 2010, in corresponding application No. 04 729 502.7.
Israeli Office Action (1 page) mailed Aug. 17, 2009, in corresponding application No. 171332.

* cited by examiner

*Primary Examiner*—Brenda L Coleman
(74) *Attorney, Agent, or Firm*—Finnegan, Henderson, Farabow, Garrett & Dunner LLP

(57) ABSTRACT

A novel 4,4-difluoro-1,2,3,4-tetrahydro-5H-1-benzazepine derivative or a pharmaceutically acceptable salt thereof, which is useful as an agent for treating or preventing nocturia and/or diabetes insipidus, is provided.

22 Claims, No Drawings

4,4-DIFLUORO-1,2,3,4-TETRAHYDRO-5H-1-BENZAZEPINE DERIVATIVE OR SALT THEREOF

This is a continuation of application Ser. No. 10/544,150, filed Oct. 21, 2005, Now U.S. Pat. No. 7,183,271 now allowed, which is the National Stage of International Application No. PCT/JP04/05998, filed Apr. 26, 2004, which claims benefit of JP2003-123032, filed Apr. 28, 2003, and JP2003-401126, filed Dec. 1, 2003, all of which are incorporated herein by reference.

TECHNICAL FIELD

This invention relates to a medicament, particularly a novel 4,4-difluoro-1,2,3,4-tetrahydro-5H-1-benzazepine derivative or a salt thereof useful as a therapeutic agent for central diabetes insipidus and nocturia, and a medicament which uses said compound as the active ingredient.

BACKGROUND OF THE INVENTION

Arginine vasopressin (AVP) is a peptide consisting of 9 amino acids which is biosynthesized and secreted in the hypothalamo-pituitary system. The receptor of AVP is classified into three subtypes $V_{1a}$, $V_{1b}$ and $V_2$, and a $V_{1a}$ receptor-mediated constriction action and a $V_2$ receptor-mediated antidiuretic action are known as the main pharmacological actions of AVP in the peripheral system. As a $V_2$ receptor-selective agonist, a peptide desmopressin (prepared by deleting amino group of the 1-position cysteine of AVP, and converting the 8-position arginine into d form) has been synthesized and used for the treatment of central diabetes insipidus (Non-patent Reference 1). However, since bioavailability of oral preparations of desmopressin is considerably low, a high dose is necessary for obtaining its effect. Thus, the desmopressin preparations are expensive, and generation of side effects based on the variation of absorption among individuals is observed in some cases. Accordingly, concern has been directed toward the development of a non-peptide antidiuretic agent which selectively stimulates $V_2$ receptor and has high bioavailability.

On the other hand, accompanied by the diversification of medical treatment and advance of age, single use of a drug became rather rare, and in many cases, two or more drugs are administered simultaneously or intermittently. This is the same in the field of AVP receptor agonists. Drugs are inactivated and converted into metabolites by undergoing the action of drug metabolizing enzymes, and the most important among these drug metabolizing enzymes is cytochrome P450 (CYP). A large number of molecular species exists in CYP, and when two or more drugs which are metabolized by CYP of the same molecular species compete on the metabolizing enzyme, it is considered that they undergo a certain metabolic inhibition, though it varies depending on the affinity of the drugs for CYP. As a result, increase of blood concentration, prolongation of blood half-life and the like drug interactions are expressed.

Such drug interactions are undesirable actions except for the case in which they are used aiming at the additive action or synergistic action, because they sometimes cause unexpected side effects. Thus, concern has been directed toward the creation of a medicament which has a low affinity for CYP and a small possibility of causing drug interactions.

Up to now, tricyclic compounds represented by a general formula (A), a general formula (B) and a general formula (C) are known as non-peptide compounds which are $V_2$ receptor-selective agonists and show antidiuretic action (Patent Reference 1, Patent Reference 2, Patent Reference 3).

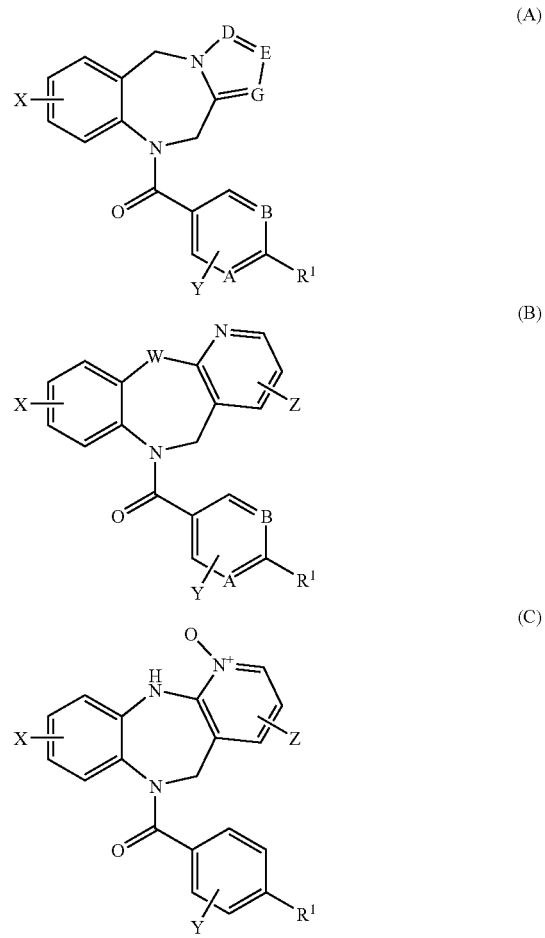

(See said patent references for signs in the formulae.)

Also, a condensed azepine derivative represented by a general formula (D) is known as a $V_2$ receptor-selective agonist (Patent Reference 4).

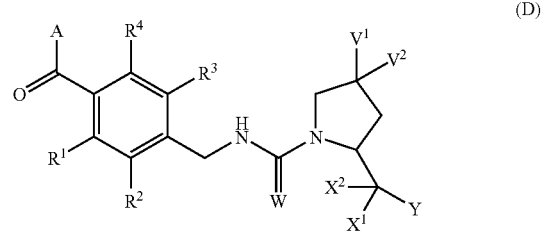

(See said patent reference for signs in the formula.)

In addition, benzazepine derivatives represented by a general formula (E) (Patent Reference 5, Patent Reference 6) and benzo-hetero ring compounds represented by a general formula (F) or a general formula (G) (Patent Reference 7, Patent Reference 8, Patent Reference 9) are known as $V_2$ receptor-selective agonists.

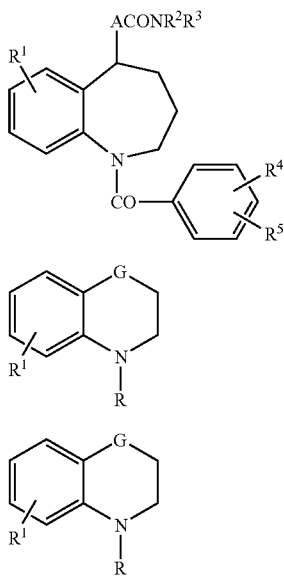

(See said patent references for signs in the formulae.)

However, there is no description in any of these patent references regarding the 4,4-difluoro-1,2,3,4-tetrahydro-5H-1-benzazepine derivative of the invention.

Also, though 4,4-difluoro-1,2,3,4-tetrahydro-5H-1-benzazepine derivative having antagonism for the AVP receptor or oxytocin receptor are known, nothing is known about their relation to $V_2$ receptor agonistic action, central diabetes insipidus and nocturia (Patent Reference 10, Patent Reference 11, Patent Reference 12). In this connection, Patent Reference 10 and Patent Reference 12 does not disclose the 4,4-difluoro-1,2,3,4-tetrahydro-5H-1-benzazepine derivative of the invention in which $CF_3$ or halogen is substituted to the 2-position benzoyl substituting on the 1-position of benzazepine. In addition, Patent Reference 11 discloses only a compound in which an aromatic ring is directly bonded to a heteroaryl group bonding to the carbonyl substituting on the 1-position of benzazepine, but does not disclose the 4,4-difluoro-1,2,3,4-tetrahydro-5H-1-benzazepine derivative of the invention in which the ring bonding to the carbonyl substituting on the 1-position of benzazepine has —O—, —S—, —NH— or a substituent group containing —N(lower alkyl)-.

Under such a situation, great concern has been directed toward the development of a non-peptide antidiuretic agent having high bioavailability, for the purpose of treating central diabetes insipidus and/or nocturia.

[Non-patent Reference 1] *Journal of Japan Endocrine Society*, 54, 676-691,

[Patent Reference 1] International Publication No. 99/06409

[Patent Reference 2] International Publication No. 99/06403

[Patent Reference 3] International Publication No. 00/46224

[Patent Reference 4] International Publication No. 01/49682

[Patent Reference 5] International Publication No. 97/22591

[Patent Reference 6] Japanese Patent No. 2926335

[Patent Reference 7] Japanese Patent No. 3215910

[Patent Reference 8] Japanese Patent publication JP-A-11-349570

[Patent Reference 9] Japanese Patent publication JP-A-2000-351768

[Patent Reference 10] International Publication No. 95/06035

[Patent Reference 11] International Publication No. 98/39325

[Patent Reference 12] Japanese Patent publication JP-A-9-221475

DISCLOSURE OF THE INVENTION

The present inventors have conducted intensive studies on a compound having $V_2$ receptor agonistic action, from which effectiveness for central diabetes insipidus and/or nocturia can be expected, and found that a novel 4,4-difluoro-1,2,3,4-tetrahydro-5H-1-benzazepine derivative has excellent said effect, thereby accomplishing the invention. In addition, it was found that the compound of the invention has markedly low inhibitory activity upon drug metabolizing enzymes CYP3A4 and CYP2C9 in comparison with conventionally known benzazepine derivatives having $V_2$ receptor agonistic action.

That is, according to the invention, there are provided a novel 4,4-difluoro-1,2,3,4-tetrahydro-5H-1-benzazepine derivative represented by the following general formula (I) or a pharmaceutically acceptable salt thereof which is useful as a therapeutic agent for central diabetes insipidus and/or nocturia; and a medicament which uses any one of these compounds as an active ingredient; particularly the aforementioned medicament which is an arginine vasopressin $V_2$ receptor agonist; and the aforementioned medicament which is a nocturia treating agent or a central diabetes insipidus treating agent.

(I)

[Signals in the formula mean as follows $R^1$: amino which may be substituted, —OH or -lower alkyl, $R^2$: $CF_3$ or halogen, $R^3$: H or halogen, a, b: each represents single bond or double bond, wherein one is single bond and the other is double bond,

—X—:

(1) —CH═CH—, —CH═N—, —N═CH—, —N═N— or —S— when a is single bond and b is double bond, (2) —N— when a is double bond and b is single bond, Y:
(1) CH or N when a is single bond and b is double bond,
(2) S when a is double bond and b is single bond, -A-: —O—, —S—, —NH— or —N(lower alkyl), and B: lower alkyl, lower alkenyl, lower alkynyl, cycloalkyl or aryl, each of which may be substituted.)

The compound of the invention has a chemical structural characteristic in which it has difluoro group on the ring carbon atom adjacent to the benzazepine ring carbon atom where a substituted methylidene group is substituted, which is completely different from the structures of conventionally known V₂ receptor-selective agonists. In this connection, since the compound of the invention has difluoro group, the double bond conjugated to carbonyl group is not isomerized, so that it has sufficient stability within an organism.

Among these compounds, preferred are novel 4,4-difluoro-1,2,3,4-tetrahydro-5H-1-benzazepine derivatives represented by the aforementioned general formula (I) in which R¹ is a group represented by a formula (II), a formula (III), —OH or —O-lower alkyl, or pharmaceutically acceptable salts thereof, and preferred among them is a novel 4,4-difluoro-1,2,3,4-tetrahydro-5H-1-benzazepine derivatives represented by the aforementioned general formula (I) in which R¹ is a group represented by the formula (II) or the formula (III), or a pharmaceutically acceptable salt thereof.

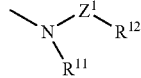
(II)

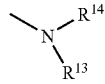
(III)

[Signs in the formulae mean as follows

Z¹: single bond, lower alkylene or -lower alkylene-C(=O)—,

R¹¹: lower alkyl which may be substituted with a group selected from the group consisting of —OH, —O-lower alkyl, —CO₂H, —CO₂-lower alkyl and carbamoyl which may be substituted with one or two lower alkyls, or —H, R¹²:
(1) when Z¹ represents single bond or lower alkylene, —H, —OH, —O-lower alkyl, —CO₂H, —CO₂-lower alkyl, carbamoyl which may be substituted with one or two lower alkyls, aryl which may be substituted, cycloalkyl which may be substituted, aromatic hetero ring which may be substituted or non-aromatic hetero ring which may be substituted,
(2) when Z¹ represents -lower alkylene-C(=O)—, a group represented by the formula (III) or a formula (IV)

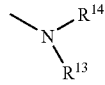
(III)

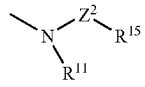
(IV)

[signs in the formula mean as follows

Z²: single bond or lower alkylene, and

R¹⁵: —H, —OH, —O-lower alkyl, —CO₂H, —CO₂-lower alkyl, carbamoyl which may be substituted with one or two lower alkyl, aryl which may be substituted, cycloalkyl which may be substituted, aromatic hetero ring which may be substituted or non-aromatic hetero ring which may be substituted, R¹³, R¹⁴: together with the adjacent nitrogen atom, non-aromatic cyclic amino group.]

More desirable is a novel 4,4-difluoro-1,2,3,4-tetrahydro-5H-1-benzazepine derivative represented by the aforementioned general formula (I), wherein R¹ is a group represented by the formula (II) or formula (III); a is a single bond; b is double bond; —X— is —CH=CH—; and —Y— is —CH—, or a pharmaceutically acceptable salt thereof.

Further desirable is a novel 4,4-difluoro-1,2,3,4-tetrahydro-5H-1-benzazepine derivative represented by the aforementioned general formula (I), wherein R¹ is a group represented by the formula (II); a is single bond; b is double bond; —X— is —CH=CH—; and —Y— is —CH—, or a pharmaceutically acceptable salt thereof.

Particularly desirable is a novel 4,4-difluoro-1,2,3,4-tetrahydro-5H-1-benzazepine derivative represented by the aforementioned general formula (I), wherein R¹ is a group represented by the formula (II); a is single bond; b is double bond; —X— is —CH=CH—; —Y— is —CH—; and -A- is —O—, or a pharmaceutically acceptable salt thereof.

Most desirable is a novel 4,4-difluoro-1,2,3,4-tetrahydro-5H-1-benzazepine derivative represented by the aforementioned general formula (I), wherein R¹ is a group represented by the formula (II); a is single bond; b is double bond; —X— is —CH=CH—; —Y— is —CH—, -A- is —O—; and —B is lower alkyl which may be substituted, or a pharmaceutically acceptable salt thereof.

Among them, a novel 4,4-difluoro-1,2,3,4-tetrahydro-5H-1-benzazepine derivative wherein R² is trifluoromethyl; and R³ is —H or —F, or a pharmaceutically acceptable salt thereof, is particularly desirable.

Particularly desirable compounds among these compounds are compounds selected from the group consisting of a compound group P and a compound group Q, or pharmaceutically acceptable salts thereof, and preferred among them are compounds selected from the compound group P, or pharmaceutically acceptable salts thereof.

In this case, the "compound group P" is a group consisting of (2Z)-N-(2-amino-2-oxoethyl)-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetamide, (2Z)-N-(2-hydroxyethyl)-2-{4,4,7-trifluoro-1-[4-{[(2S)-2-fluoropropyl]oxy}-2-(trifluoromethyl)benzoyl]-1,2,3,4-tetrahydro-5H-1-benzazepin-5-ylidene}acetamide, (2Z)-N-(2-hydroxyethyl)-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetamide, (2Z)-2-{4,4-difluoro-1-[4-{[(2R)-2-fluoropropyl]oxy}-2-(trifluoromethyl)benzoyl]-1,2,3,4-tetrahydro-5H-1-benzazepin-5-ylidene}-N-[(2S)-2,3-dihydroxypropyl]acetamide, 3-[((2Z)-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetyl)amino]propanamide, and (2Z)-N-[(2R)-2,3-dihydroxypropyl]-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetamide, and the "compound group Q" is a group consisting of (2Z)-N-(2-amino-2-oxoethyl)-2-{4,4,7-trifluoro-1-[4-{[(2S)-2-fluoropropyl]oxy}-2-(trifluoromethyl)benzoyl]-1,2,3,4-tetrahydro-5H-1-benzazepin-5-ylidene}acetamide, (2Z)-2-{1-[4-(2,2-difluoropropoxy)-2-(trifluoromethyl)benzoyl]-4,4-difluoro-1,2,3,4-tetrahydro-5H-1-benzazepin-5-ylidene}-N-(2-hydroxyethyl)acetamide, (2Z)-2-{4,4-difluoro-1-[4-{[(2S)-2-fluoropropyl]oxy}-2-(trifluoromethyl)benzoyl]-1,2,3,4-tetrahydro-5H-1-benzazepin-5-ylidene}-N-(2-hydroxyethyl)acetamide, (2Z)-2-{4,4-difluoro-1-[4-{[(2R)-2-fluoropropyl]oxy}-2-(trifluoromethyl)benzoyl]-1,2,3,4-tetrahydro-5H-1-benzazepin-5-ylidene}-N-(2-hydroxyethyl)acetamide, (2Z)-2-{1-[4-(2,2-difluoropropoxy)-2-(trifluoromethyl)benzoyl]-4,4,7-trifluoro-1,2,3,4-tetrahydro-5H-1-benzazepin-5-ylidene}-N-(2-hydroxyethyl)acetamide, (2Z)-N-[(2R)-2,3-dihydroxypropyl]-2-{4,4,7-trifluoro-1-[4-propoxy-2-(trifluoromethyl)benzoyl]-1,2,3,4-tetrahydro-5H-1-benzazepin-5-ylidene}acetamide, (2Z)-2-{4,4-difluoro-1-[4-{[(2S)-2-fluoropropyl]oxy}-2-(trifluoromethyl)benzoyl]-1,2,3,4-tetrahydro-5H-1-benzazepin-5-ylidene}-N-[(2S)-2,3-dihydroxypropyl]acetamide, (2Z)-2-{4,4-difluoro-1-[4-{[(2R)-2-fluoropropyl]oxy}-2-(trifluoromethyl)benzoyl]-1,2,3,4-tetrahydro-5H-1-benzazepin-5-ylidene}-N-[(2R)-2,3-dihydroxypropyl]acetamide, 3-[((2Z)-2-{4,4,7-trifluoro-1-[4-{[(2S)-2-fluoropropyl]oxy}-2-(trifluoromethyl)benzoyl]-1,2,3,4-tetrahydro-5H-1-benzazepin-5-ylidene}acetyl)amino]propanamide, (2Z)-N-[(2R)-2,3-dihydroxypropyl]-2-{4,4,7-trifluoro-1-[4-{[(2S)-2-fluoropropyl]oxy}-2-(trifluoromethyl)benzoyl]-1,2,3,4-tetrahydro-5H-1-benzazepin-5-ylidene}acetamide, 3-[((2Z)-2-{1-[4-(2,2-difluoropropoxy)-2-(trifluoromethyl)benzoyl]-4,4,7-trifluoro-1,2,3,4-tetrahydro-5H-1-benzazepin-5-ylidene}acetyl)amino]propanamide, (2Z)-2-{4,4-difluoro-1-[4-propoxy-2-(trifluoromethyl)benzoyl]-1,2,3,4-tetrahydro-5H-1-benzazepin-5-ylidene}-N-[(2R)-2,3-dihydroxypropyl]acetamide, and (2Z)-2-{4,4-difluoro-1-[4-propoxy-2-(trifluoromethyl)benzoyl]-1,2,3,4-tetrahydro-5H-1-benzazepin-5-ylidene}-N-[(2S)-2,3-dihydroxypropyl]acetamide.

In this connection, regarding $R^1$, the group represented by the aforementioned formula (II) or the aforementioned formula (III) is desirable; the group represented by the aforementioned formula (II), wherein $Z^1$ is single bond, $R^{12}$ is —H and $R^{11}$ is lower alkyl which may be substituted, is further desirable; and the group represented by the aforementioned formula (II), wherein $Z^1$ is single bond, $R^{12}$ is —H and $R^{11}$ is lower alkyl which may be substituted with one or more substituent groups selected from a group consisting of —OH and carbamoyl, is particularly desirable.

Also, regarding $R^2$, trifluoromethyl or chloro is desirable; and trifluoromethyl is particularly desirable.

Also, regarding $R^3$, —H or fluoro is desirable; and —H or 7-fluoro is particularly desirable.

Also, regarding a, b, —X— and —Y—, it is desirable that a is single bond, b is double bond, —X— is —CH=CH—, and —Y— is —CH—.

Also, —O— is desirable as -A-.

In addition, regarding —B, lower alkyl which may be substituted is desirable; and lower alkyl which may be substituted with F is particularly desirable.

The following further describes the compound of the invention.

In this description, the "lower alkyl" means a monovalent group of straight or branched $C_{1-6}$ carbon chain, and its illustrative examples include methyl, ethyl, propyl, butyl, pentyl and hexyl, and isopropyl, tert-butyl and the like structural isomers thereof, preferably a $C_{1-4}$ alkyl methyl, ethyl, propyl, butyl and isobutyl.

The "lower alkylene" means a divalent group of straight or branched $C_{1-6}$ carbon chain, and its illustrative examples include methylene, ethylene, trimethylene, methylmethylene, methylethylene, dimethylmethylene and the like.

The "lower alkenyl" means a monovalent group of straight or branched $C_{2-6}$ carbon chain having at least one double bond, and its illustrative examples include vinyl, allyl, 1-butenyl, 2-butenyl, 1-hexenyl, and 3-hexenyl, 2-methylallyl and the like structural isomers thereof, of which allyl and 2-methyl-1-propen-3-yl are preferable.

The "lower alkynyl" means a monovalent group of straight or branched $C_{2-6}$ carbon chain having at least one triple bond, and its illustrative examples include ethynyl, propargyl, 1-butynyl, 3-butynyl, 1-hexynyl, and 3-hexynyl, 3-methyl-1-butynyl and the like structural isomers thereof, of which propargyl and 1-butyn-4-yl are preferred.

The "cycloalkyl" means a monovalent group of $C_{3-8}$ non-aromatic hydrocarbon ring which may partially have a unsaturated bond, and its illustrative examples include cyclopropyl, cyclopentyl, cyclohexyl, cyclooctyl, cyclohexenyl, cyclooctanedienyl and the like.

The "aryl" means a monovalent group of monocyclic to tricyclic $C_{6-14}$ aromatic hydrocarbon ring, and its illustrative examples include phenyl, naphthyl and the like, of which phenyl is preferably.

The "aromatic hetero ring" means a monovalent group of monocyclic to tricyclic aromatic ring having hetero atom(s) such as nitrogen, oxygen, sulfur or the like, and its illustrative examples include pyridyl, thienyl, furyl, pyrazinyl, pyridazinyl, thiazolyl, pyrimidinyl, pyrazolyl, pyrrolyl, oxazolyl, isothiazolyl, isooxazolyl, imidazolyl and the like, of which pyridyl is preferred.

The "non-aromatic hetero ring" means a monovalent group of 5- to 7-membered ring having hetero atom(s) such as nitrogen, oxygen, sulfur or the like, which may partially have an unsaturated bond and may be condensed with aryl or aromatic hetero ring, and its illustrative examples include pyrrolidinyl, imidazolidinyl, piperidinyl, piperazinyl, azepinyl, morphonyl, thiomorphonyl, tetrahydrofuryl, tetrahydrothienyl and the like, of which pyrrolidinyl, piperidinyl and morphonyl are preferable.

The "non-aromatic cyclic amino group" means a monovalent group of 3- to 10-membered non-aromatic cyclic amine, preferably 5- to 7-membered non-aromatic cyclic amine, having nitrogen, oxygen or sulfur, which may partially have an unsaturated bond, and its illustrative examples include pyrrolidinyl, piperidinyl, azepinyl, morphonyl, thiomorphonyl, piperazinyl, pyrazolidinyl, dihydropyrrolyl and the like, of which pyrrolidinyl, piperidinyl, piperazinyl and morphonyl are preferred.

The "halogen" means a monovalent group of halogen atom, and its illustrative examples include fluoro, chloro, bromo, iodo and the like.

According to this description, the acceptable substituent group regarding the term "which may be substituted" may be any substituent group which is generally used as the substituent group of respective group, and each group may have one or more substituent groups.

Regarding the "amino which may be substituted" in $R^1$, the groups represented by the aforementioned general formulae (II) and (III) can be illustratively exemplified.

The groups shown by the following (a) to (h) can be exemplified as acceptable substituent groups of "cycloalkyl which may be substituted" and "aryl which may be substituted" in B; "aryl which may be substituted", "cycloalkyl which may be substituted", "aromatic hetero ring which may be substituted" and "non-aromatic hetero ring which may be substituted" in $R^{12}$ and $R^{15}$; and "non-aromatic amino group which may be substituted" in $R^{13}$ and $R^{14}$. In this connection, $R^Z$ represents a lower alkyl which may be substituted with one or more groups selected from the class consisting of —OH, —O-lower alkyl, amino which may be substituted with 1 or 2 lower alkyl, carbamoyl which may be substituted with 1 or 2 lower alkyl, aryl, aromatic hetero ring and halogen.

(a) Halogen;

(b) —OH, —O—$R^Z$, —O-aryl, —OCO—$R^Z$, oxo (=O);

(c) —SH, —S—$R^Z$, —S-aryl, —SO—$R^Z$, —SO-aryl, —$SO_2$—$R^Z$, —$SO_2$-aryl, sulfamoyl which may be substituted with 1 or 2 $R^Z$;

(d) amino which may be substituted with 1 or 2 $R^Z$, —NHCO—$R^Z$, —NHCO-aryl, —$NHSO_2$—$R^Z$, —$NHSO_2$-aryl, nitro;

(e) —HO, —CO—$R^Z$, —$CO_2H$, —$CO_2$—$R^Z$, carbamoyl which may be substituted with 1 or 2 $R^Z$, cyano;

(f) aryl or cycloalkyl which may be respectively substituted with one or more groups selected from the class consisting of —OH, —O-lower alkyl, amino which may be substituted with 1 or 2 lower alkyl, carbamoyl which may be substituted with 1 or 2 lower alkyl, aryl, aromatic hetero ring, halogen and $R^Z$;

(g) aromatic hetero ring or non-aromatic hetero ring which may be respectively substituted with one or more groups selected from the class consisting of —OH, —O-lower alkyl, amino which may be substituted with 1 or 2 lower alkyl, carbamoyl which may be substituted with 1 or 2 lower alkyl, aryl, aromatic hetero ring, halogen and $R^Z$; and (h) lower alkyl or lower alkenyl which may be respectively substituted with one or more groups selected from the substituent groups shown in the aforementioned (a) to (g).

The groups shown in the aforementioned (a) to (g) can be exemplified as the acceptable substituent groups of "lower alkyl which may be substituted", "lower alkenyl which may be substituted" and "lower alkynyl which may be substituted" in B.

Depending on the kind of substituent groups, compounds of the invention represented by the general formula (I) sometimes contain asymmetric carbon atom, and optical isomers based thereon can be present therein. All of the mixtures and isolates of these optical isomers are included in the invention. Also, tautomers are present in the compounds of the invention in some cases, and isolates or mixtures of these isomers are included in the invention.

Also, the compounds of the invention sometimes form salts, and such salts are included in the invention with the proviso that they are pharmaceutically acceptable salts. Their illustrative examples include acid addition salts with hydrochloric acid, hydrobromic acid, hydroiodic acid, sulfuric acid, nitric acid phosphoric acid and the like inorganic acids or with formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, glutamic acid and the like organic acids, salts with inorganic bases including sodium, potassium, calcium, magnesium and the like metals or with methylamine, ethylamine, ethanolamine, lysine, ornithine and the like organic bases, ammonium salts and the like. In addition, various hydrates, solvates and substances having polymorphism of the compounds of the invention and pharmaceutically acceptable salts thereof are also included in the invention. In this connection, all of the compounds which are converted into compounds having the aforementioned general formula (I) or salts thereof by undergoing metabolism in the living body, so-called prodrugs, are also included in the invention. Regarding groups which form prodrugs of the invention, the groups described in *Prog. Med.,* 5; 2157-2161, 1985 and the groups described in "Iyakuhin no Kaihatsu" (Development of Medicines), vol. 7, Bunshi Sekkei (Molecular Design), pp. 163-198, published in 1990 by Hirokawa Shoten can be exemplified.

(Production Methods)

The compounds of the invention and pharmaceutically acceptable salts thereof can be produced by employing various conventionally known synthesis methods, making use of characteristics based on their basic nuclei or the kind of substituent groups. Typical production methods are exemplified in the following. In this connection, depending on the kind of functional group, it is effective in some cases, in view of production techniques, to replace said functional group with an appropriate protecting group, namely a group which is easily converted into said functional group, at a stage of from the materials to intermediates. Thereafter, the compound of interest can be obtained by removing the protecting group as occasion demands. Examples of such a functional group include hydroxyl group, carboxy group, amino group and the like, and the protecting groups described in "Protective Groups in Organic Synthesis (3rd Edition)" edited by Greene and Wuts can be exemplified as their protecting groups which may be optionally used in response to the reaction conditions.

<Intermediate Production Method>

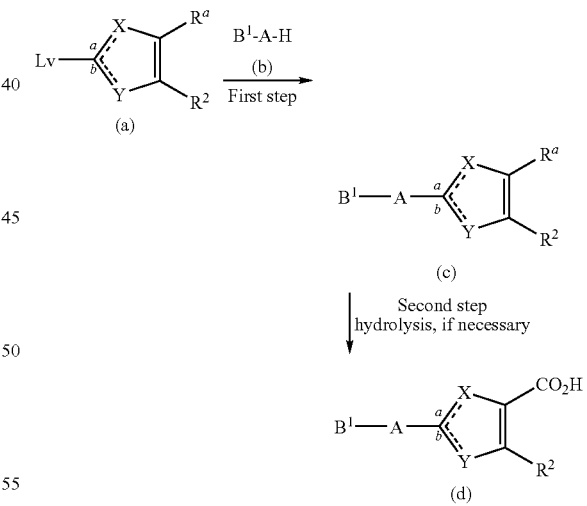

(In the reaction scheme, $R^2$, a, b, X, Y and A are as defined in the foregoing; Lv represents a leaving group; $B^1$ represents the aforementioned B or a protecting group of hydroxyl group, amino group or sulfanil group; $R^a$ represents caboxyl group, a lower alkyl oxycarbonyl group or cyano group. The same shall apply hereinafter.)

This production method is a method in which the compound (c) is produced by substituting leaving group Lv of the compound (a) by the compound (b), and then the compound (d) is produced therefrom by carrying out hydrolysis of the same as occasion demands.

11

(First Step)

Examples of the leaving group Lv in the compound (a) include fluoro, chloro, methanesulfonyloxy, p-toluenesulfonyloxy and trifluoromethanesulfonyloxy, of which fluoro, chloro and methanesulfonyloxy are preferred.

The reaction can be carried out at room temperature to heating under reflux using the compound (a) and compound (b) in equimolar amounts or one of them in an excess amount, without solvent or in a reaction inert solvent such as benzene, toluene, xylene or the like aromatic hydrocarbons; diethyl ether, tetrahydrofuran (THF), dioxane or the like ethers; dichloromethane, 1,2-dichloroethane, chloroform or the like halogenated hydrocarbons; N,N-dimethylformamide (DMF); dimethylacetamide (DMA); N-methylpyrrolidone; dimethyl sulfoxide (DMSO); ethyl acetate (EtOAc) or the like esters; acetonitrile or the like, or in methanol (MeOH), ethanol (EtOH), 2-propanol (iPrOH) or the like alcohols. Depending on the compound, it is advantageous in some cases to carry out the reaction in the presence of an organic base (preferably triethylamine, diisopropylethylamine, N-methylmorpholine, pyridine or 4-(N,N-dimethylamino) pyridine) or a metal salt base (preferably potassium carbonate, cesium carbonate, sodium hydroxide or sodium hydride).

(Second Step)

The reaction can be carried out by treating the compound (c) under cooling to heating under reflux, in a solvent inert to the reaction such as an aromatic hydrocarbon, an ether, a halogenated hydrocarbon, an alcohol solvent, DMF, DMA, DMSO, pyridine, water or the like in the presence of sulfuric acid, hydrochloric acid, hydrobromic acid or the like mineral acid, formic acid, acetic acid or the like organic acid or sodium hydroxide, potassium hydroxide, potassium carbonate, sodium carbonate, cesium carbonate, ammonia or the like base.

<First Production Method>

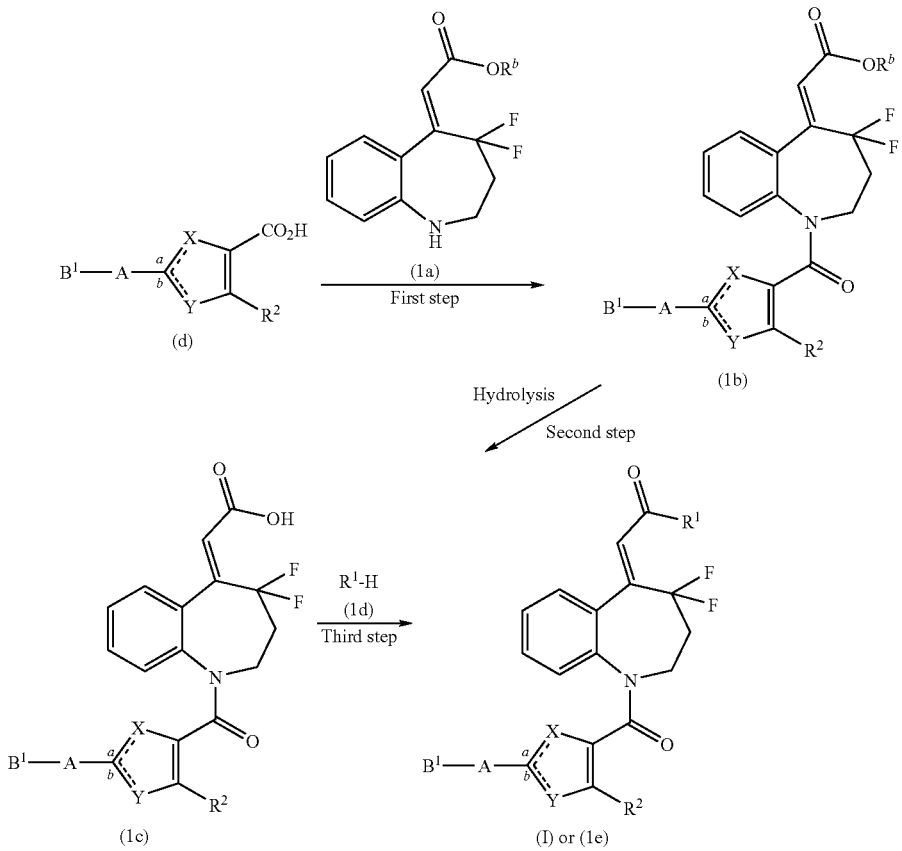

(In the reaction scheme, $R^1$ is as defined in the foregoing, and $R^b$ represents a lower alkyl. The same shall apply hereinafter.)

This production method is a method in which a compound (1b) is produced by condensing the compound (d) produced in the aforementioned intermediate production method with a compound (1a), a compound (1c) is produced by hydrolyzing the former and then the product is condensed with a compound (1d), thereby producing the compound (I) of the invention in which $B^1$ is B or a compound (1e) in which $B^1$ is hydroxyl group, amino group or sulfanil group.

(First Step)

The compound (d) can be used in the reaction as free acid, but its reactive derivative can also be used in the reaction. Examples of the reactive derivative of compound (d) include methyl ester, ethyl ester, tert-butyl ester or the like general ester; acid chloride, acid bromide or the like acid halide; acid azide; active ester with N-hydroxybenzotriazole, p-nitrophenol, N-hydroxysuccinimide or the like; symmetric acid anhydride; mixed acid anhydride with alkyl carbonate halide or the like halocarboxylic acid alkyl ester, pivaloyl halide, p-toluenesulfonic acid chloride or the like; mixed acid anhydride such as a phosphoric acid system mixed acid anhydride obtained by reacting with diphenylphosphoryl chloride and N-methylmorpholine, and the like.

When the compound (d) is allowed to undergo the reaction as free acid, or an active ester is allowed to undergo the reaction without isolation, it is desirable to use a condensing agent such as dicyclohexylcarbodiimide (DCC), 1,1'-carbonylbis-1H-imidazole (CDI), diphenylphosphoryl azide (DPPA), diethylphosphoryl cyanide, 1-ethyl-3-(3-dimethylaminopropyl)carbodiimide hydrochloride (WSCD) or the like.

According to the invention, an acid chloride method, a method in which the reaction is carried out in the coexistence of an active esterification agent and a condensing agent and a method in which a general ester is treated with amine are particularly convenient, because the compound of the invention can be obtained conveniently and easily.

Though it varies depending on the reactive derivative and condensing agent to be used, the reaction is carried out under cooling, under cooling to room temperature or under room temperature to heating, in a reaction inert solvent such as a halogenated hydrocarbon, an aromatic hydrocarbon, an ether, an ester, acetonitrile, DMF, DMSO or the like.

In this connection, it is advantageous in some cases in smoothly progressing the reaction to use the compound (1a) in an excess amount in carrying out the reaction, or to carry out the reaction in the presence of a base such as N-methylmorpholine, trimethylamine, triethylamine, diisopropylethylamine, N,N-dimethylaniline, pyridine, 4-(N,N-dimethylamino)pyridine, picoline, rutidine or the like. In addition, a salt consisting of pyridine hydrochloride, pyridine p-toluenesulfonate, N,N-dimethylaniline hydrochloride or the like weak base and a strong acid may be used. Pyridine can also be used as a solvent.

Particularly, it is suitable to carry out the reaction in acetonitrile, DMF or the like solvent in the presence of pyridine, N,N-dimethylaniline or the like base or pyridine hydrochloride or the like salt.

(Second Step)

The reaction can be carried out in accordance with the second step of the intermediate production method.

(Third Step)

The reaction can be carried out in accordance with the first step of the first production method.

The compound (1e) can be made into the compound (I) of the invention by removing the protecting group as occasion demands or further introducing a necessary side chain in accordance with a general method. Introduction of the necessary side chain can also be carried out in accordance with the third step of the following second production method.

<Second Production Method>

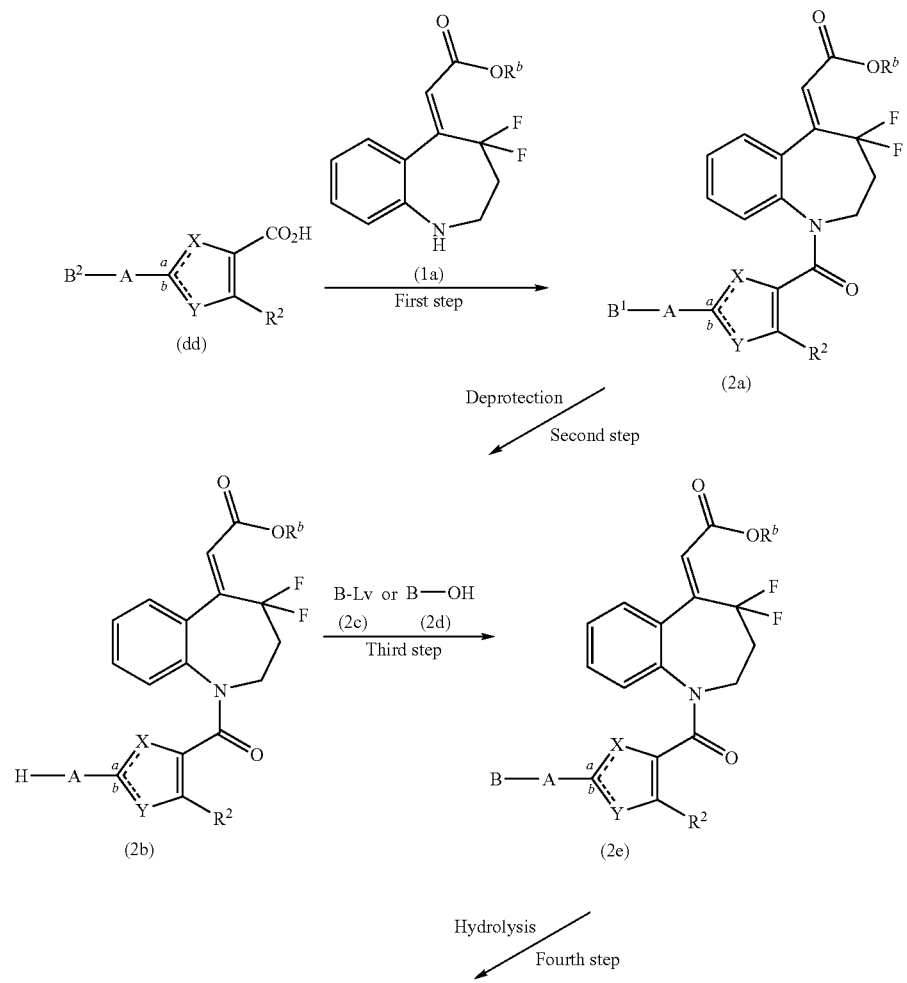

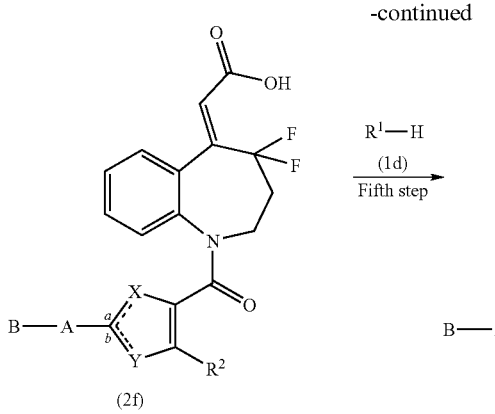

(In the reaction scheme, $B^2$ is protecting group of hydroxyl group, amino group or sulfanil group. The same shall apply hereinafter.)

This production method is a method in which a compound (2a) is produced by condensing a compound (dd) produced by the aforementioned intermediate production method, wherein $B^2$ is not B, with a compound (1a), a compound (2b) is produced by removing the protecting group $B^2$, a compound (2f) is produced by condensing with a compound (2c) or (2d), a compound (2f) is produced by hydrolyzing it, and then the compound (I) of the invention is produced by condensing with a compound (1d).

(First Step)

This reaction can be carried out in accordance with the first step of the first production method.

(Second Step)

As the protecting group of hydroxyl group, amino group or sulfanil group, the protecting groups described in the aforementioned "Protective Groups in Organic Synthesis (3rd Edition)" can be exemplified. The reaction can be carried out in accordance with the method described in "Protective Groups in Organic Synthesis (3rd Edition)".

Particularly, when benzyl group is used as the protecting group of hydroxyl group, a method in which benzyl group is removed by allowing pentamethylbenzene to react therewith in a strongly acidic solution such as trifluoroacetic acid or the like can also be used.

(Third Step)

As the leaving group Lv in the compound (2c), chloro, bromo, iodo, methanesulfonyloxy, p-toluenesulfonyloxy and trifluoromethanesulfonyloxy can for example be cited, of which bromo, methanesulfonyloxy and p-toluenesulfonyloxy are preferable.

Regarding the reaction which uses the compound (2c), a general alkylation reaction can be used, and preferably, it can be carried out using the compound (2b) and compound (2c) under cooling, under cooling to room temperature or under room temperature to heating in equimolar amounts or one of them in an excess amount in a reaction inert solvent such as acetonitrile, DMF, DMSO, an ether or the like, in the presence of potassium carbonate, sodium carbonate, cesium carbonate, sodium hydroxide, potassium hydroxide or the like base.

The reaction which uses the compound (2d) can be carried out under the Mitsunobu reaction condition in an aprotic solvent reaction inert to the reaction, such as an ether, DMF, N-methylpyrrolidone or the like, in the presence of triphenylphosphine or the like organic phosphine and diethyl azodicarboxylate, diisopropyl azodicarboxylate or the like dialkyl azodicarboxylate (*Synthesis*, 1981, p. 1).

(Fourth Step)

This reaction can be carried out in accordance with the second step of the first production method.

(Fifth Step)

This reaction can be carried out in accordance with the first step of the first production method.

In addition, some of the compounds of the invention represented by the formula (I) can be produced from the compounds of the invention obtained by the first production method or second production method, by optionally combining conventionally known alkylation, acylation, substitution reaction, oxidation, reduction, hydrolysis and the like steps which can be generally employed by those skilled in the art. Illustratively, oxidation of sulfur atom by metachloroperbenzoic acid or the like oxidizing agent, and the like can for example be cited, and such reactions carried out by employing or in accordance with the methods described in "Jikken Kagaku Koza (Experimental Chemistry Course) 4th edition" (Maruzen, 1990-1992). In addition, these steps which can be generally employed by those skilled in the art are not limited to the application to the compounds of the invention, and they can also be applied to the production intermediates. Illustratively, they can be applied, for example, to the compound obtained by the third step of the second production method, and thereafter, the next step can be carried out.

The compounds of the invention produced in this manner are isolated and purified as free compounds or salts thereof by carrying out salt formation treatment in the usual way. Isolation and purification are carried out by employing usual chemical operations such as extraction, concentration, evaporation, crystallization, filtration, recrystallization, various types of chromatography and the like.

Various isomers can be isolated in the usual way by making use of differences in physicochemical properties among isomers. For example, a racemic mixture can be converted into optically pure isomers, for example, by a general racemic body resolution method such as a method in which they are converted into diastereomer salts with tartaric acid or the like general optically active acid and then subjected to optical resolution. Also, a diastereomer mixture can be separated, for example, by fractional crystallization or various types of chromatography. In addition, an optically active compound can also be produced using an appropriate optically active material.

INDUSTRIAL APPLICABILITY

The compounds of the invention have excellent agonistic activity upon arginine vasopressin $V_2$ receptor. Accordingly, the compounds of the invention have antidiuretic action of a profile based on this action, and are effective in preventing and/or treating urinary frequency, urinary incontinence, enuresis, central diabetes insipidus, nocturia and nocturnal enuresis. Also, in addition to these, since they have the action to release blood coagulation factor VIII and von Willebrand factor based on the $V_2$ receptor agonistic activity, they are useful for various bleeding conditions and useful in diagnosing, preventing and treating spontaneous hemorrhage, hemophilia, von Willebrand disease, uremia, congenital or acquired platelet dysfunction, traumatic and operation hemorrhage, hepatic cirrhosis and the like.

In addition, the compounds of the invention have markedly low inhibitory activity upon drug metabolizing enzymes CYP3A4 and CYP2C9, possibility of causing drug interaction with other drugs which are metabolized via CYP3A4 or CYP2C9 is small in comparison with the conventionally known benzazepine derivatives having arginine vasopressin $V_2$ receptor agonistic activity, so that they are also excellent from the viewpoint that they can be safely used in the combined therapy with other medicaments.

Examples of the drugs which are metabolized by CYP3A4 include simvastatin, lovastatin, fluvastatin, midazolam, nifedipine, amlodipine, nicardipine and the like, and examples of the drugs which are metabolized by CYP2C9 include diclofenac, ibuprofen, indometacin, tolbutamide, glibenclamide, losartan and the like (*Sogo Rinsho* (General Clinics), 48(6), 1427-1431, 1999).

Pharmacological actions of the compounds of the invention were verified by the following test methods.

(1) $V_2$ Receptor Binding Test

A human $V_2$ expression CHO cell membrane sample was prepared in accordance with the method of Tahara et al. (*British Journal of Pharmacology*, Vol. 125, pp. 1463-1470, 1998). A 2 µg portion of the membrane sample was incubated together with [$^3$H]-arginine vasopressin (to be referred simply to as "[$^3$H]-vasopressin" hereinafter) (0.5 nM, specific activity=75 Ci/mmol) and each compound to be tested ($10^{-10}$ to $10^{-5}$ M) at 25° C. for 60 minutes in 250 µl in total volume of 50 mM Tris-HCl buffer (pH=7.4) containing 10 mM $MgCl_2$ and 0.1% bovine serum albumin (BSA). Thereafter, free [$^3$H]-vasopressin and receptor-bonded [$^3$H]-vasopressin were separated using a cell harvester, and the receptor-bonded [$^3$H]-vasopressin was adhered onto a uni-filter plate GF/B glass filter. After sufficient drying, this was mixed with a microplate scintillation cocktail, amount of the receptor-bonded [$^3$H]-vasopressin was measured using top count and the inhibition ratio was calculated by the following formula.

Inhibition ratio(%)=100−($C_1$−$B_1$)/($C_0$−$B_1$)×100

$C_1$: Amount of [$^3$H]-vasopressin bonded to the membrane sample when [$^3$H]-vasopressin and the receptor membrane sample are treated in the coexistence of test compound having known concentration $C_0$: Amount of [$^3$H]-vasopressin bonded to the membrane sample when [$^3$H]-vasopressin and the receptor membrane sample are treated in the absence of test compound $B_1$: Amount of [$^3$H]-vasopressin bonded to the membrane sample when [$^3$H]-vasopressin and the receptor membrane sample are treated in the coexistence of excess amount of vasopressin ($10^{-6}$ M)

Concentration of each test compound by which the inhibition ratio becomes 50% ($IC_{50}$ value) was calculated by the aforementioned formula, and affinity of the test compound for the receptor, namely dissociation constant (Ki), was calculated from this by the following formula.

Dissociation constant(*Ki*)=$IC_{50}$/(1+[*L*]/*Kd*)

[L]: Concentration of [$^3$H]-vasopressin

Kd: Dissociation constant of [$^3$H]-vasopressin against the receptor obtained by a saturation binding test

TABLE 1

| Affinity for $V_2$ receptor | | | |
|---|---|---|---|
| Compounds | Ki (nM) | Compounds | Ki (nM) |
| Example 3 | 11 | Example 31 | 10 |
| Example 9 | 19 | Example 54 | 17 |
| Example 14 | 18 | Example 55 | 16 |
| Example 24 | 4.3 | Example 134 | 12 |
| Example 46 | 5.8 | Example 136 | 11 |
| Example 98 | 6.2 | Comparative compound | 68 |

In this connection, the comparative compound is the compound of Example 32 described in International Publication WO 97/22591 (compound name: 2-[(5R)-1-(2-chloro-4-pyrrolidin-1-ylbenzoyl)-2,3,4,5-tetrahydrobenzazepin-5-yl]-N-isopropylacetamide).

As shown in Table 1, it was confirmed that the compounds of the invention have high affinity for $V_2$ receptor.

(2) Antidiuretic Test (Intravenous Administration)

Five animals per group of male Wistar rats (10 to 12 weeks of age) were used in the test. The compound of Example 3 was intravenously administered to group A at a dose of 0.3 mg/kg, and the compound of Example 9 to group B at a dose of 0.3 mg/kg, both after dissolving in a solvent (physiological saline containing DMSO), and the solvent alone at a dose of 1 ml/kg to group C as a control, and then 30 ml/kg of distilled water was orally administered by force 15 minutes thereafter (water loading). Urine samples until 2 hours after the water loading were collected using a metabolism cage, and the amount of urine when the water loading amount was defined as 100% was calculated as the urine excretion ratio. In this connection, average value of the urine excretion ratio until after 1 hour and the urine excretion ratio until after 2 hours in each group was used in the evaluation. The results are shown in Table 2.

TABLE 2

| Antidiuretic effects (intravenous administration) | | | |
|---|---|---|---|
| | | Urine excretion ratio (%) | |
| | Compounds | After 1 hour | After 2 hours |
| Group A | Example 3 | 1.3 | 6.2 |
| Group B | Example 9 | 0 | 5.3 |
| Group C | Solvent | 64.0 | 80.0 |

As shown in Table 2, it was revealed that the compounds of the invention have excellent antidiuretic effects.

(3) Antidiuretic Test (Oral Administration)

Male Wistar rats (10 to 12 weeks of age) were used in the test. Each compound to be tested was orally administered, and then 30 ml/kg of distilled water was orally administered by force 15 minutes thereafter (water loading). Urine samples until 4 hours after the water loading were collected using a metabolism cage, and the amount of urine when the water loading amount was defined as 100% was calculated as the urine excretion ratio. In this connection, the dose each test compound necessary for reducing 50% of the urine excretion ratio ($ED_{50}$) was used in the evaluation. As a result, it was revealed that the compounds of the invention show excellent antidiuretic action not only by intravenous administration but also by oral administration.

(4) Cytochrome P450 (3A4) Enzyme Inhibition Test

This test was carried out in accordance with the method of Crespi et al. (*Analytical Biochemistry*, 248, 188-190, 1997).

Using a 96 well plate, 7-benzyloxy-4-(trifluoromethyl)cumarin as the substrate ($5 \times 10^{-5}$ M), each test compound (from $4.9 \times 10^{-8}$ to $5 \times 10^{-5}$ M) and the enzyme ($5 \times 10^{-9}$ M) were incubated at 37° C. for 30 minutes in 200 μl in total volume of 200 mM phosphate buffer (pH=7.4) containing 8.2 μM NADP+, 0.41 mM glucose-6-phosphate, 0.41 mM $MgCl_2$ and 0.4 units/ml glucose-6-phosphate dehydrogenase. Thereafter, the reaction was stopped by adding 0.5 M 2-amino-2-hydroxymethyl-1,3-propanediol aqueous solution containing 80% acetonitrile, and the fluorescence intensity (excitation wavelength; 409 nm, fluorescence wavelength; 530 nm) was measured using a fluorescence plate reader. The inhibition ratio was calculated based on the following formula, and concentration of each test compound by which the inhibition ratio becomes 50% ($IC_{50}$) was obtained. The results are shown in Table 3.

Inhibition ratio (%)=$100-(C_1-B_1)/(C_0-B_1) \times 100$ $C_1$: Fluorescence intensity in the presence of test compound having known concentration, enzyme and substrate $C_0$: Fluorescence intensity in the absence of test compound and in the presence of enzyme and substrate $B_1$: Fluorescence intensity of blank well (5) Cytochrome P450 (2C9) Enzyme Inhibition Test This test was carried out in accordance with the method of Crespi et al. (*Analytical Biochemistry*, 248, 188-190, 1997).

Using a 96 well plate, 7-methoxy-4-(trifluoromethyl)cumarin as the substrate ($7.5 \times 10^{-5}$ M), each test compound (from $4.9 \times 10^{-8}$ to $5 \times 10^{-5}$ M) and the enzyme ($10^{-8}$ M) were incubated at 37° C. for 45 minutes in 200 μl in total volume of 200 mM phosphate buffer (pH=7.4) containing 8.2 μM NADP+, 0.41 mM glucose-6-phosphate, 0.41 mM $MgCl_2$ and 0.4 units/ml glucose-6-phosphate dehydrogenase. Thereafter, the reaction was stopped by adding 0.5 M 2-amino-2-hydroxymethyl-1,3-propanediol aqueous solution containing 80% acetonitrile, and the fluorescence intensity (excitation wavelength; 409 nm, fluorescence wavelength; 530 nm) was measured using a fluorescence plate reader. The inhibition ratio was calculated based on the same formula of aforementioned (4), and concentration of each test compound by which the inhibition ratio becomes 50% ($IC_{50}$) was obtained. The results are shown in Table 3.

TABLE 3

| CYP (3A4 and 2C9) inhibitory activity | | |
|---|---|---|
| | $IC_{50}$ (μM) | |
| Compounds | CYP3A4 | CYP2C9 |
| Example 3 | >50 | >50 |
| Example 9 | 13 | 11 |
| Example 51 | >50 | 34 |

TABLE 3-continued

| CYP (3A4 and 2C9) inhibitory activity | | |
|---|---|---|
| | $IC_{50}$ (μM) | |
| Compounds | CYP3A4 | CYP2C9 |
| Example 54 | >50 | 43 |
| Example 130 | >50 | >50 |
| Example 136 | >50 | >50 |
| Comparative compound | <0.091 | <0.091 |

As shown in Table 3, the compounds of the invention showed markedly low inhibitory action upon the drug metabolizing enzymes CYP3A4 and CYP2C9. In this connection, the comparative compound is the same comparative compound shown in Table 1.

The medicament of the invention can be prepared by a generally used method using one or more of the compounds of the invention represented by the general formula (I) and carriers for drug, fillers and other additive agents which are generally used in preparing medicines. Its administration may be either oral administration in the form of tablets, pills, capsules, granules, powders, solutions and the like, or parenteral administration in the form of intravenous injections, intramuscular injections or the like injections, or suppositories, transnasal preparations, transmucosal preparations, percutaneous preparations and the like.

The solid composition for use in the oral administration according to the present invention is used in the form of tablets, powders, granules and the like. In such a solid composition, one or more active substances are mixed with at least one inert diluent such as lactose, mannitol, glucose, hydroxypropylcellulose, microcrystalline cellulose, starch, polyvinyl pyrrolidone, aluminum magnesium silicate or the like. In the usual way, the composition may contain other additives than the inert diluent, such as magnesium stearate or the like lubricant, calcium cellulose glycolate or the like disintegrating agent, lactose or the like stabilizing agent and glutamic acid, aspartic acid or the like solubilization assisting agent. As occasion demands, tablets or pills may be coated with a sugar coating a film of a gastric or enteric substance, such as sucrose, gelatin, hydroxypropylcellulose, hydroxypropylmethylcellulose phthalate or the like.

The liquid composition for oral administration includes pharmaceutically acceptable emulsions, solutions, suspensions, syrups, elixirs and the like and contains a generally used inert diluent such as purified water or ethanol. In addition to the inert diluent, this composition may also contain a moistening agent, a suspending agent and the like auxiliary agents, as well as sweeteners, flavors, aromatics and antiseptics.

The injections for parenteral administration includes aseptic aqueous or non-aqueous solutions, suspensions and emulsions. Examples of the diluent for use in the aqueous solutions and suspensions include distilled water for injection and physiological saline. Examples of the diluent for use in the non-aqueous solutions and suspensions include propylene glycol, polyethylene glycol, olive oil or the like plant oil, EtOH or the like alcohol, polysorbate 80 and the like. Such a composition may further contain additive agents including an antiseptic, a moistening agent, an emulsifying agent, a dispersing agent, a stabilizing agent such as lactose, and a solubilization assisting agent such as glutamic acid or aspartic acid. These are sterilized, for example, by filtration through a bacteria retaining filter, blending of a germicide or irradiation. Alternatively, they can also be used by firstly making into sterile solid compositions and dissolving them in sterile water or a sterile solvent for injection prior to their use.

In the case of oral administration, the appropriate daily dose is generally from about 0.0001 to 50 mg/kg, preferably from about 0.001 to 10 mg/kg, more preferably from 0.01 to 1 mg/kg, per body weight, and this is administered once a day or dividing it into 2 to 4 doses. In the case of intravenous administration, the appropriate daily dose is generally from about 0.0001 to 1 mg/kg, preferably from about 0.0001 to 0.1 mg/kg, per body weight, and this is administered once a day or dividing it into two or more doses. The dose is optionally decided in response to individual cases by taking into consideration symptoms, age, sex and the like. However, since the dose varies under various conditions, a smaller dose than the above range may be sufficient enough in some cases.

BEST MODE FOR CARRYING OUT THE INVENTION

The following illustratively describes the invention based on examples, but the invention is not restricted by these examples. In this connection, since novel substances are included in the material compounds to be used in the examples, methods for producing such material compounds from conventionally known substances are described as reference examples.

Reference Example 1

A 5.2 g portion of 60% sodium hydride oil dispersion was suspended in 50 ml of DMF, and 6.73 ml of benzyl alcohol was added thereto under ice-cooling. After warming up to room temperature, 12.3 g of 4-fluoro-2-trifluoromethylbenzoic acid was added thereto and stirred at room temperature for 6 hours. A 1 M hydrochloric acid aqueous solution was added to the reaction mixture, and the thus precipitated crystals were collected by filtration to obtain 16.39 g of 4-(benzyloxy)-2-(trifluoromethyl)benzoic acid.

MS(+); 297

In the same manner as in Reference Example 1, Reference Examples 2 to 4 shown in Table 4 were produced using respective corresponding materials.

In this connection, signs in the table show the following meanings (the same shall apply hereinafter).

Rf: Reference Example number,

Data: physicochemical date (NMR: uses $(CH_3)_4Si$ as the internal standard, and unless otherwise noted, shows peak δ (ppm) by $^1$H-NMR using DMSO-$d_6$ as the measuring solvent, MS(+): FAB-MS [M+H]$^+$, MS(−): FAB-MS [M−H]$^+$, EMS(+): ESI-MS [M+H]$^+$, EMS(−): ESI-MS [M−H]$^+$, $R^A$, $R^B$: substituent groups in the general formula, nPr: normal propyl, cPr: cyclopropyl.

In this connection, regarding the NMR data, there is a case in which a compound gives a complex data due to the presence of two or more conformers, but among them, only a peak which corresponds to a conformer considered to be mainly present was described. In addition, these peaks were converged on a peak showing one kind of compound, by measuring under heating.

Table 4

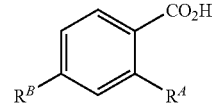

| Rf | $R^A$ | $R^B$ | Data |
|----|-------|-------|------|
| 2 | $CF_3$ | cPr—$CH_2$O— | EMS(−): 259 |
| 3 | Cl | nPr—S— | MS(+): 231 |
| 4 | $CF_3$ | nPr—S— | MS(−): 263 |

Reference Example 5

A 4.44 g portion of methyl 4-fluoro-2-trifluorobenzoate was dissolved in 40 ml of DMF, 3.32 g of potassium carbonate and 4.10 ml of N-methyl-N-propylamine were added thereto, and the mixture was stirred at 80° C. for 14 hours. After cooling the reaction mixture, phase separation operation was carried out by adding water and EtOAc. The organic layer was washed with saturated brine and dried with anhydrous sodium sulfate, and then the crude product obtained by evaporating the solvent was subjected to a silica gel column chromatography, eluted with hexane-EtOAc (4:1) and concentration under a reduced pressure to obtain 4.79 g of methyl 4-[methyl(propyl)amino]-2-(trifluoromethyl)benzoate.

MS(+): 276

Reference Example 6

A 4.78 g portion of the compound of Reference Example 5 was dissolved in 20 ml of MeOH, and 6.94 g of 5 M sodium hydroxide aqueous solution was added thereto and stirred at 70° C. for 5 hours. The reaction mixture was cooled and then concentrated under a reduced pressure. The thus obtained residue was neutralized with 1 M hydrochloride acid aqueous solution, and the precipitated crystals were collected by filtration to obtain 4.36 g of 4-[methyl(propyl)amino]-2-(trifluoromethyl)benzoic acid.

MS(+): 262

Reference Example 7

A 8.0 g portion of the compound of Reference Example 1 was dissolved in 80 ml of THF, 8 ml of thionyl chloride and 3 drops of DMF were added thereto under ice-cooling, and then this was stirred at room temperature for 3 hours. By evaporating the reaction solvent and then carrying out drying, an acid chloride compound was obtained. This was mixed with 6.84 g of (Z)-methyl (4,4-difluoro-1,2,3,4-tetrahydro-5H-1-benzazepin-5-ylidene)acetate, mixed with 50 ml of pyridine under ice-cooling and then stirred at room temperature for 12 hours. After completion of the reaction, the solvent was evaluated and separation of layers was carried out by adding 1 M hydrochloric acid aqueous solution and EtOAc. The organic layer was washed with water and saturated brine and dried with anhydrous sodium sulfate. The solvent was evaporated and the thus obtained residue was recrystallized from EtOH to obtain 9.12 g of methyl (2Z)-{1-[4-(benzyloxy)-2-(trifluoromethyl)benzoyl]-4,4-difluoro-1,2,3,4-tetrahydro-5H-1-benzazepin-5-ylidene}acetate.

EMS(+): 532

In the same manner as in Reference Example 7, the Reference Examples 8 to 11 shown in Table 5 were produced using respective corresponding materials.

In this connection, the sign in the table represents the following meaning (the same shall apply hereinafter).

Me: methyl.

Table 5

[Structure: benzazepine with CO2Me ylidene, difluoro, N-benzoyl with R^A and R^B substituents]

| Rf | R^A | R^B | Data |
|---|---|---|---|
| 8 | $CF_3$ | cPr—$CH_2$O— | EMS(+): 496 |
| 9 | Cl | nPr—S— | MS(+): 466 |
| 10 | $CF_3$ | nPr—S— | MS(+): 500 |
| 11 | $CF_3$ | nPr—N(Me)— | MS(+): 497 |

Reference Example 12

A 9.1 g portion of the compound of Reference Example 7 was dissolved in 100 ml of trifluoroacetic acid, and 5.1 g of pentamethylbenzene was added thereto and stirred at room temperature for 12 hours. The insoluble matter was filtered, and then the filtrate was concentrated under a reduced pressure. Diethyl ether was added to the thus obtained residue, and the precipitated crystals were collected by filtration to obtain 6.22 g of methyl (2Z)-{4,4-difluoro-1-[4-(benzyloxy)-2-(trifluoromethyl)benzoyl]-1,2,3,4-tetrahydro-5H-1-benzazepin-5-ylidene}acetate.

EMS(+): 442

Reference Example 7

A 3.89 g portion of the compound of Reference Example 12 was dissolved in 20 ml of DMSO, and 2.06 g of tert-butyl bromoacetate and 1.46 g of potassium carbonate were added thereto and stirred at room temperature for 2 hours. After filtration of the insoluble matter, separation of layers was carried out by adding water and EtOAc. The organic layer was washed with saturated brine and dried with anhydrous sodium sulfate. The solvent was evaporated and the thus obtained residue was subjected to a silica gel column chromatography to obtain 3.55 g of methyl (2Z)-{1-[4-(2-tert-butoxy-2-oxoethoxy)-2-(trifluoromethyl)benzoyl]-4,4-difluoro-1,2,3,4-tetrahydro-5H-1-benzazepin-5-ylidene}acetate from chloroform-MeOH (80:1) eluate.

EMS(+): 556

Reference Example 14

A 3.75 g portion of the compound of Reference Example 13 was dissolved in 20 ml of trifluoroacetic acid and stirred at room temperature for 30 minutes. By evaporating the solvent under a reduced pressure, 3.25 g of [4-{[(5Z)-4,4-difluoro-5-(2-methoxy-2-oxoethylidene)-2,3,4,5-tetrahydro-1H-1-benzazepin-1-yl]carbonyl}-3-(trifluoromethyl)phenoxy]acetic acid was obtained.

MS(+): 450

Reference Example 15

A 1.09 g portion of the compound of Reference Example 14 was dissolved in 10 ml of DMF, 324 mg of HOBt, 460 mg of WSCD, 1.20 ml of dimethylamine (2.0 M THF solution) and 0.335 ml of triethylamine were added thereto, and then this was stirred at room temperature for 6 hours. Sodium bicarbonate aqueous solution was added to the reaction liquid, the thus formed precipitate was collected by filtration, and the thus obtained crude product was washed with water and then dried under a reduced pressure to obtain 1.14 g of methyl (2Z)-{1-[4-(2-dimethylamino-2-oxoethoxy)-2-(trifluoromethyl)benzoyl]-4,4-difluoro-1,2,3,4-tetrahydro-5H-1-benzazepin-5-ylidene}acetate.

MS(+): 527

Reference Example 16

A 1.00 g portion of the compound of Reference Example 12 was dissolved in 15 ml of THF, 0.415 ml of 1-butanol, 1.19 g of triphenylphosphine and 2.08 ml of diethyl azodicarboxylate were added thereto, and then this was stirred at room temperature for 17 hours. Water and EtOAc were added to the reaction mixture to carry out separation of layers. The organic layer was washed with water and saturated brine and dried with anhydrous magnesium sulfate. The solvent was evaporated and the thus obtained residue was subjected to a silica gel column chromatography, eluted with chloroform-MeOH (50:1) and then concentrated under a reduced pressure to obtain 1.41 g of crude methyl (2Z)-{1-[4-butoxy-2-(trifluoromethyl)benzoyl]-4,4-difluoro-1,2,3,4-tetrahydro-5H-1-benzazepin-5-ylidene}acetate.

The compound obtained in the above was dissolved in 5 ml MeOH-10 ml THF, mixed with 1 M sodium hydroxide aqueous solution and then stirred at room temperature for 2 hours. After evaporation of the solvent, 1 M hydrochloric acid and chloroform-iPrOH (3:1 mixed solvent) was added thereto to carry out separation of layers. The organic layer was washed with saturated brine and dried with anhydrous sodium sulfate. By evaporating the solvent, 1.01 g of (2Z)-{1-[4-butoxy-2-(trifluoromethyl)benzoyl]-4,4-difluoro-1,2,3,4-tetrahydro-5H-1-benzazepin-5-ylidene}acetic acid was obtained.

MS(+): 484

In the same manner as in Reference Example 16, the Reference Examples 17 to 19 shown in Table 6 were produced using respective corresponding materials.

In this connection, the sign in the table represents the following meaning (the same shall apply hereinafter).

iBu: isobutyl.

Table 6

[Structure: benzazepine with CO2H ylidene, difluoro, N-benzoyl with R^A and R^B substituents]

| Rf | R^A | R^B | Data |
|---|---|---|---|
| 17 | $CF_3$ | nPr—O— | MS(+): 470 |
| 18 | $CF_3$ | iBu—O— | MS(+): 483 |
| 19 | Cl | iBu—O— | MS(+): 450 |

Reference Example 40

A 1.43 g portion of the compound of Reference Example 7 was dissolved in a mixed solvent of 15 ml MeOH-25 ml THF, mixed with 1 M sodium hydroxide aqueous solution and stirred at room temperature for 2 hours. After evaporation of the solvent, the liquid property was changed to acidic by adding 1 M hydrochloric acid, and then the thus precipitated white solid was collected by filtration and dried under a reduced pressure to obtain 1.39 g of (2Z)-{1-[4-(benzyloxy)-2-(trifluoromethyl)benzoyl]-4,4-difluoro-1,2,3,4-tetrahydro-5H-1-benzazepin-5-ylidene}acetic acid.

MS(+): 518

In the same manner as in Reference Example 20, the Reference Examples 21 to 25 shown in Table 7 were produced using respective corresponding materials.

Table 7

| Rf | $R^A$ | $R^B$ | Data |
|---|---|---|---|
| 21 | $CF_3$ | CPr—$CH_2$O— | EMS(+): 482 |
| 22 | Cl | nPr—S— | MS(+): 452 |
| 23 | $CF_3$ | nPr—S— | MS(+): 486 |
| 24 | $CF_3$ | nPr—N(Me)— | MS(+): 483 |
| 25 | $CF_3$ | $Me_2NOCCH_2$—O— | MS(+): 513 |

Reference Example 26

Concentrated sulfuric acid was added to MeOH solution of the compound of Reference Example 1, and heating under reflux was carried out for 3 days. The reaction mixture was poured into ice water to carry out extraction operation with ether. After evaporation of the solvent, the thus obtained residue was dissolved in EtOH, mixed with 10% palladium on carbon and, in an atmosphere of hydrogen, stirred at room temperature for 24 hours to obtain methyl 4-hydroxy-2-(trifluoromethyl)benzoate.

MS(+): 221

Reference Example 27

Bromoacetone and potassium carbonate was added to acetonitrile solution of the compound of Reference Example 26 and stirred at 60° C. for 1 hour to obtain methyl 4-(2-oxopropoxy)-2-(trifluoromethyl)benzoate.

ESI-MS(+): 299 [M+23]$^+$

Reference Example 28

(Diethylamino)sulfur trifluoride was added at −78° C. to methylene chloride solution of the compound of Reference Example 27, and stirred at room temperature for 24 hours to obtain methyl 4-(2,2-difluoropropoxy)-2-(trifluoromethyl)benzoate.

EI-MS: 298 [M]$^+$

Reference Example 29

5 M Sodium hydroxide aqueous solution was added to MeOH solution of the compound of Reference Example 28, and stirred at 90° C. for 2.5 hours to obtain 4-(2,2-difluoropropoxy)-2-(trifluoromethyl)benzoic acid.

MS(−): 283

Reference Example 30

Triethylamine was added to methylene chloride solution of (2S)-propane-1,2-diol, and then methylene chloride solution of p-toluenesulfonyl chloride was added thereto at −20° C. and stirred at room temperature for 18 hours to obtain (2S)-2-hydroxypropyl-4-methylbenzene sulfonate.

MS(+): 231

Reference Example 30A

N,N-Dimethylaniline and acetic anhydride were added to THF solution of the compound of Reference Example 30 and stirred at 0° C. for 1 hour to obtain (1S)-1-methyl-2-{[(4-methylphenyl)sulfonyl]oxy}ethyl acetate.

MS(+): 273

Reference Example 30B

The compound of Reference Example 26 and potassium carbonate were added to DMF solution of the compound of Reference Example 30A and stirred at 70° C. for 17 hours to obtain methyl 4-{[(2S)-2-(acetyloxy)propyl]oxy}-2-(trifluoromethyl)benzoate.

MS(+): 321

Reference Example 31

1 M Potassium hydroxide-MeOH solution was added at 0° C. to MeOH solution of the compound of Reference Example 30B and stirred at room temperature for 1 hour to obtain methyl 4-{[(2S)-2-hydroxypropyl]oxy}-2-(trifluoromethyl)benzoate.

MS(+): 279

Reference Example 32

(Diethylamino)sulfur trifluoride was added at −78° C. to methylene chloride solution of the compound of Reference Example 31 and stirred at room temperature for 15 hours to obtain methyl 4-{[(2R)-2-fluoropropyl]oxy}-2-(trifluoromethyl)benzoate.

FAB-MS(+): 280 [M]$^+$

Reference Example 33

5 M Sodium hydroxide aqueous solution was added to MeOH solution of the compound of Reference Example 32 and stirred at 70° C. for 6 hours to obtain 4-{[(2R)-2-fluoropropyl]oxy}-2-(trifluoromethyl)benzoic acid.

MS(+): 267

Reference Example 34

Sodium borohydride was added at 0° C. to EtOH solution of the compound of Reference Example 27 and stirred at room temperature for 1 hour to obtain methyl 4-(2-hydroxypropoxy)-2-(trifluoromethyl)benzoate.

ESI-MS(+): 301 [M+23]$^+$

Reference Example 35

In the same manner as in Reference Example 30, (2R)-2-hydroxypropyl-4-methylbenzene sulfonate was produced using (2R)-propane-1,2-diol.
MS(+): 231

Reference Example 35A

In the same manner as in Reference Example 30A, (1R)-1-methyl-2-{[(4-methylphenyl)sulfonyl]oxy}ethyl acetate was produced using the compound of Reference Example 35.
MS(+): 273

Reference Example 35B

In the same manner as in Reference Example 30B, methyl 4-{[(2R)-2-(acetyloxy)propyl]oxy}-2-(trifluoromethyl)benzoate was produced using the compound of Reference Example 35A.
MS(+): 321

Reference Example 36

In the same manner as in Reference Example 31, methyl 4-{[(2R)-2-hydroxypropyl]oxy}-2-(trifluoromethyl)benzoate was produced using the compound of Reference Example 35B.
MS(+): 279

Reference Example 37

In the same manner as in Reference Example 32, methyl 4-{[(2S)-2-fluoropropyl]oxy}-2-(trifluoromethyl)benzoate was produced using the compound of Reference Example 36.
MS(+): 281

Reference Example 38

In the same manner as in Reference Example 33, 4-{[(2S)-2-fluoropropyl]oxy}-2-(trifluoromethyl)benzoic acid was produced using the compound of Reference Example 37.
MS(+): 267

In the same manner as in Reference Example 7, the Reference Examples 39 to 41 shown in Table 8 were produced using respective corresponding materials.

Table 8

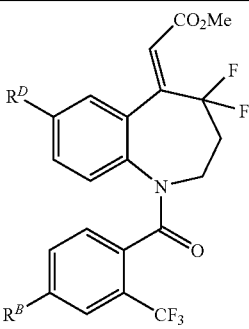

| Rf | $R^B$ | $R^D$ | Data |
|---|---|---|---|
| 39 | (S)—O—CH$_2$CHFCH$_3$ | H | EMS(+): 502 |
| 39A | (R)—O—CH$_2$CHFCH$_3$ | H | EMS(+): 502 |
| 40 | (S)—O—CH$_2$CHFCH$_3$ | F | MS(+): 520 |
| 40A | (R)—O—CH$_2$CHFCH$_3$ | F | MS(+): 520 |
| 41 | —O—CH$_2$CF$_2$CH$_3$ | H | MS(+): 520 |

In the same manner as in Reference Example 20, the Reference Examples 42 to 46 shown in Table 9 were produced using respective corresponding materials.

Table 9

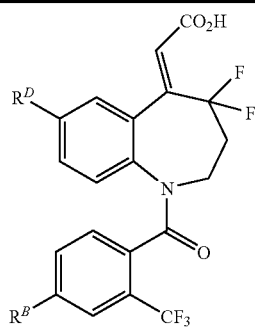

| Rf | $R^B$ | $R^D$ | Data |
|---|---|---|---|
| 42 | (S)—O—CH$_2$CHFCH$_3$ | H | MS(+): 488 |
| 43 | (R)—O—CH$_2$CHFCH$_3$ | H | MS(+): 488 |
| 44 | (S)—O—CH$_2$CHFCH$_3$ | F | MS(+): 506 |
| 45 | (R)—O—CH$_2$CNFCH$_3$ | F | MS(+): 506 |
| 46 | —O—CH$_2$CF$_2$CH$_3$ | H | MS(+): 506 |

Example 1

A 150 mg portion of the compound of Reference Example 20 was dissolved in 5 ml of DMF, mixed with 43 mg of HOBt, 61 mg of WSCD, 35 mg of glycine amide hydrochloride and 0.045 ml of triethylamine, and then stirred at room temperature for 4 hours. Saturated sodium bicarbonate aqueous solution and EtOAc were added to the reaction mixture to carry out separation of layers. The organic layer was washed with water and saturated brine and dried with anhydrous magnesium sulfate. The solvent was evaporated, and the thus obtained residue was recrystallized from EtOH to obtain 139 mg of (2Z)-N-(2-amino-2-oxoethyl)-2-{1-[4-(benzyloxy)-2-(trifluoromethyl)benzoyl]-4,4-difluoro-1,2,3,4-tetrahydro-5H-1-benzazepin-5-ylidene}acetamide.

In the same manner as in Example 1, the Examples 2 to 16 as shown in Table 10 were produced using respective corresponding materials.

Example 17

A 150 mg portion of the compound of Example 20 was dissolved in 3.5 ml of THF, mixed with 0.3 ml of thionyl chloride and 2 to 3 drops of DMF and stirred at room temperature for 1 hour. The solvent was evaporated under a reduced pressure, and thionyl chloride was further removed by azeotropic evaporation using toluene. The thus obtained residue was dissolved in THF, and this solution was added dropwise to aqueous ammonia. Separation of layers was carried out by adding EtOAc to the reaction mixture. The organic layer was washed with saturated brine and then dried with anhydrous magnesium sulfate. The thus obtained crude product was recrystallized from iPrOH-diisopropyl ether mixed solvent to obtain 126 mg of (2Z)-2-{1-[4-(benzyloxy)-2-(trifluoromethyl)benzoyl]-4,4-difluoro-1,2,3,4-tetrahydro-5H-1-benzazepin-5-ylidene}acetamide.

In the same manner as in Example 17, the Example 18 as shown in Table 10 was produced using respective corresponding materials. Also, in the same manner as in Reference Example 12, the Examples 19 and 20 as shown in Table 10 were produced using respective corresponding materials.

Example 21

A 325 mg portion of the compound of Example 6 was dissolved in 5 ml of 1,2-dichloroethane, mixed with 148 mg of m-chlorobenzoic acid under ice-cooling, and stirred at room temperature for 4 hours. The reaction mixture was mixed with 10% (w/v) $Na_2S_2O_3 \cdot 5H_2O$ aqueous solution, water and chloroform to carry out separation of layers. The organic layer was washed with saturated sodium bicarbonate aqueous solution and dried with anhydrous sodium sulfate, the solvent was evaporated, and then the thus obtained crude product was subjected to a silica gel column chromatography, eluted with chloroform-MeOH (23:2) and concentrated under a reduced pressure to obtain 121 mg of (2Z)-N-(2-amino-2-oxoethyl)-2-{4,4-difluoro-1-[4-(propylsulfinyl)benzoyl]-1,2,3,4-tetrahydro-5H-1-benzazepin-5-ylidene}acetamide.

In the same manner as in Example 21, the Example 22 as shown in Table 10 was produced using respective corresponding materials. Also, the Examples 23 to 147 as shown in Tables 11 to 18 were produced using respective corresponding materials, by the aforementioned production methods or the methods described in Examples, or methods obvious to those skilled in the art or modified methods thereof.

In this connection, signs in the tables represent the following meanings (the same shall apply hereinafter).

Ex: example number, $R^C$: substituent group in the general formula,

Et: ethyl, nBu: normal butyl, Ph: phenyl, Py: pyridyl, Bn: benzyl, Gly: carbamoylmethylamino ($-NHCH_2CONH_2$), Etha: 2-hydroxyethylamino ($-NHCH_2CH_2OH$), Car: amino ($-NH_2$). In this connection, the numeral before each substituent group resents the substituting position. Illustratively, for example, —NHPh(2-OH) means 2-hydroxyphenylamino, and —NHCH$_2$(2-Py) means pyridine-2-ylmethylamino.

Table 10

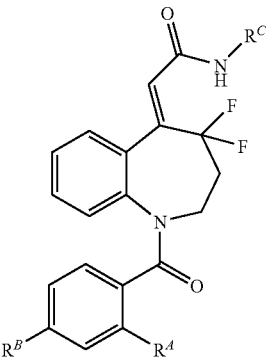

| Ex | $R^A$ | $R^B$ | $R^C$ | MS(+) |
|---|---|---|---|---|
| 1 | —CF$_3$ | Bn—O— | —CH$_2$—CONH$_2$ | 574 |
| 2 | —CF$_3$ | Bn—O— | —(CH$_2$)$_2$—OH | 561 |
| 3 | —CF$_3$ | cPr—CH$_2$O— | —CH$_2$—CONH$_2$ | 538 |
| 4 | —CF$_3$ | cPr—CH$_2$O— | —(CH$_2$)$_2$—OH | 525 |
| 5 | —Cl | nPr—S— | —CH$_2$—CONH$_2$ | 508 |
| 6 | —CF$_3$ | nPr—S— | —CH$_2$CONH$_2$ | 542 |
| 7 | —CF$_3$ | nPr—O— | —CH$_2$CONH$_2$ | 526 |
| 8 | —CF$_3$ | nPr—O— | —(CH$_2$)$_2$—OH | 513 |
| 9 | —CF$_3$ | nBu—O— | —CH$_2$—CONH$_2$ | 540 |
| 10 | —CF$_3$ | nBu—O— | —(CH$_2$)$_2$—OH | 527 |
| 11 | —CF$_3$ | iBu—O— | —CH$_2$—CONH$_2$ | 540 |
| 12 | —CF$_3$ | iBu—O— | —(CH$_2$)$_2$—OH | 527 |
| 13 | —Cl | iBu—O— | —CH$_2$—CONH$_2$ | 506 |
| 14 | —CF$_3$ | nPr—N(Me)— | —CH$_2$—CONH$_2$ | 539 |

Table 10-continued

| Ex | $R^A$ | $R^B$ | $R^C$ | MS(+) |
|---|---|---|---|---|
| 15 | —CF$_3$ | Me$_2$NOCCH$_2$—O— | —CH$_2$—CONH$_2$ | 569 |
| 16 | —CF$_3$ | nPr—O— | —H | 469 |
| 17 | —CF$_3$ | Bn—O— | —H | 517 |
| 18 | —CF$_3$ | nPr—N(Me)— | —H | 482 |
| 19 | —CF$_3$ | HO— | —CH$_2$—CONH$_2$ | 484 |
| 20 | —CF$_3$ | HO— | —H | 427 |
| 21 | —CF$_3$ | nPr—S(=O)— | —CH$_2$CONH$_2$ | 558 |
| 22 | —CF$_3$ | nPr—S(=O)$_2$— | —CH$_2$—CONH$_2$ | 574 |

Table 11

| Ex | $R^B$ | $R^D$ | MS(+) |
|---|---|---|---|
| 23 | —OnPr | F | 544 |
| 24 | —OnPr | Cl | 560 |
| 25 | —OnPr | Br | 604,606 |
| 26 | —O—CH$_2$C(CH$_3$)=CH$_2$ | H | 538 |
| 27 | —O—(CH$_2$)CH$_2$F | H | 544 |
| 28 | (S)—O—CH$_2$CHFCH$_3$ | H | 544 |
| 29 | (R)—O—CH$_2$CHFCH$_3$ | H | 544 |
| 30 | (S)—O—CH$_2$CHFCH$_3$ | F | 562 |
| 31 | (R)—O—CH$_2$CHFCH$_3$ | F | 562 |
| 32 | —O—CH$_2$CHFCH$_3$ | H | 544 |
| 33 | —O—CH$_2$CF$_2$CH$_3$ | H | 562 |
| 34 | —O—CH$_2$CF$_2$CH$_3$ | F | 580 |
| 35 | —N(Me)Et | H | 525 |
| 36 | —N(Et)nPr | H | 553 |
| 37 | —N(Me)nBu | H | 553 |
| 38 | —N(Me)iBu | H | 553 |
| 39 | —NnPr$_2$ | H | 567 |
| 40 | —SEt | H | 528 |
| 41 | —SiBu | H | 556 |
| 42 | —SCH=CH$_2$ | H | 526 |
| 43 | —SCH$_2$CH$_2$F | H | 546 |
| 44 | —S(CH$_2$)$_2$CH$_2$F | H | 560 |
| 45 | —SCH$_2$CHFCH$_3$ | H | 560 |

Table 12

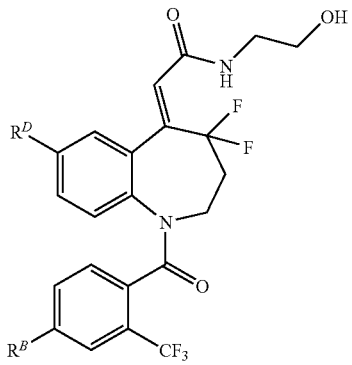

| Ex | $R^B$ | $R^D$ | MS(+) |
|---|---|---|---|
| 46 | —OnPr | F | 531 |
| 47 | —OnPr | Cl | 547 |
| 48 | —O—CH$_2$cPr | H | 525 |
| 49 | —O—(CH$_2$)$_2$CH$_2$F | H | 531 |
| 50 | —O—CH$_2$CHFCH$_3$ | H | 531 |
| 51 | —O—CH$_2$CF$_2$CH$_3$ | H | 549 |
| 52 | (S)—O—CH$_2$CHFCH$_3$ | H | 531 |
| 53 | (R)—O—CH$_2$CHFCH$_3$ | H | 531 |
| 54 | (S)—O—CH$_2$CHFCH$_3$ | F | 549 |
| 55 | (R)—O—CH$_2$CHFCH$_3$ | F | 549 |
| 56 | —O—CH$_2$CF$_2$CH$_3$ | F | 567 |
| 57 | —N(Me)(CH$_2$)$_2$CH$_2$F | H | 544 |
| 58 | —N(Et)nPr | H | 540 |
| 59 | —SCH=CH$_2$ | H | 513 |
| 60 | —SCH$_2$CH$_2$F | H | 533 |
| 61 | —S(CH$_2$)$_2$CH$_2$F | H | 547 |

Table 13

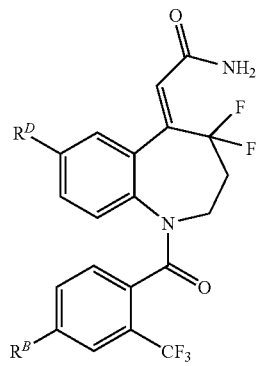

| Ex | $R^B$ | $R^D$ | MS(+) |
|---|---|---|---|
| 62 | —OnPr | F | 487 |
| 63 | —OnPr | Cl | 503 |
| 64 | —OnPr | Br | 547, 549 |
| 65 | —O—(CH$_2$)$_2$CH$_2$F | H | 487 |
| 66 | —O—CH$_2$CHFCH$_3$ | H | 487 |
| 67 | —O—CH$_2$CF$_2$CH$_3$ | H | 505 |
| 68 | —O—CH$_2$CF$_2$CH$_3$ | F | 523 |
| 69 | (S)—O—CH$_2$CHFCH$_3$ | H | 487 |
| 70 | (R)—O—CH$_2$CHFCH$_3$ | H | 487 |
| 71 | (S)—O—CH$_2$CHFCH$_3$ | F | 505 |
| 72 | (R)—O—CH$_2$CHFCH$_3$ | F | 505 |
| 73 | —N(Me)(CH$_2$)$_2$CH$_2$F | H | 500 |
| 74 | —N(Me)CH$_2$CF$_2$CH$_3$ | H | 518 |
| 75 | —N(Et)nPr | H | 496 |
| 76 | —N(Et)(CH$_2$)$_2$CH$_2$F | H | 514 |
| 77 | —NnPr$_2$ | H | 510 |

TABLE 14

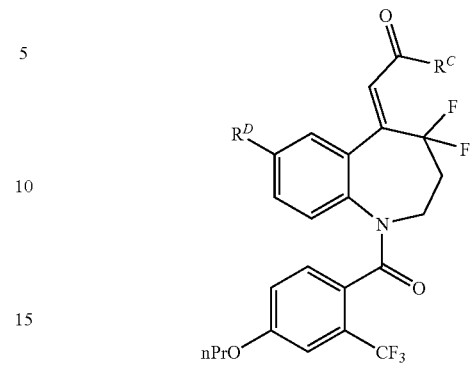

| Ex | $R^C$ | $R^D$ | MS(+) |
|---|---|---|---|
| 78 | —NH(CH$_2$)$_2$OMe | H | 527 |
| 79 | —NHC(Me)$_2$CH$_2$OH | H | 541 |
| 80 | —NH(CH$_2$)$_2$F | H | 515 |
| 81 | —NH(CH$_2$)$_3$OH | H | 527 |
| 82 | —NH(CH$_2$)$_3$F | H | 529 |
| 83 | —NHCH$_2$CH(OH)CH$_2$OH | H | 543 |
| 84 | —NHCH$_2$CH(R—OH)CH$_2$OH | H | 543 |
| 85 | —NHCH$_2$CH(S—OH)CH$_2$OH | H | 543 |
| 86 | —NHCH$_2$CH(R—OH)CH$_2$OH | F | 561 |
| 87 | —NH(CH$_2$)$_2$O(CH$_2$)$_2$OH | H | 557 |
| 88 | —NH(CH$_2$)$_2$NMe$_2$ | H | 540 |
| 89 | —NH(CH$_2$)$_2$CONH$_2$ | H | 540 |
| 90 | —NH(CH(CONH$_2$)$_2$ | H | 569 |
| 91 | —NHCH$_2$CONHMe | H | 540 |
| 92 | —NHCH$_2$CONMe$_2$ | H | 554 |
| 93 | —NH(CH$_2$)$_2$NHCOCH$_3$ | H | 554 |
| 94 | —N(CH$_2$CH$_2$OH)$_2$ | H | 557 |
| 95 | —N(CH$_2$CONH$_2$)$_2$ | H | 583 |
| 96 | —NHPh | H | 545 |
| 97 | —NHPh(2-OH) | H | 561 |
| 98 | —NHPh(3-OH) | H | 561 |
| 99 | —NHPh(4-OH) | H | 561 |
| 100 | —NHPh(2-CONH$_2$) | H | 588 |
| 101 | —NHPh(3-CONH$_2$) | H | 588 |
| 102 | —NHPh(4-CONH$_2$) | H | 588 |
| 103 | —NHPh(3-SO$_2$NH$_2$) | H | 624 |
| 104 | —NHPh(4-SO$_2$NH$_2$) | H | 624 |
| 105 | —NHPh(3-NHCOMe) | H | 602 |

TABLE 15

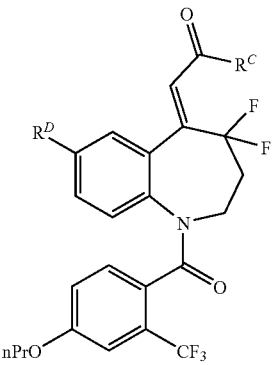

| Ex | $R^C$ | $R^D$ | MS(+) |
|---|---|---|---|
| 106 | —NHCH$_2$Ph(3-OH) | H | 575 |
| 107 | —NHCH$_2$Ph(4-OH) | H | 575 |
| 108 | —NHCH$_2$Ph(4-SO$_2$NH$_2$) | H | 638 |
| 109 | —NHCH$_2$(2-Py) | H | 560 |

TABLE 15-continued

Common structure: benzazepine with =CH-C(=O)-R^C, gem-difluoro, R^D on aromatic ring, N-acyl with 4-nPrO-2-CF3-benzoyl.

| Ex | R^C | R^D | MS(+) |
|---|---|---|---|
| 110 | CH2-NH(CH3) connected to C(=O)-pyrrolidine (glycyl pyrrolidine amide with N-methyl) | H | 580 |
| 111 | CH2-NH(CH3) connected to C(=O)-(3-hydroxypyrrolidine) | H | 596 |
| 112 | CH2-NH(CH3) connected to C(=O)-piperidine | H | 594 |
| 113 | CH2-NH(CH3) connected to C(=O)-(4-hydroxypiperidine) | H | 610 |

TABLE 16

Common structure: same as above.

| Ex | R^C | R^D | MS(+) |
|---|---|---|---|
| 114 | 1-methyl-3-hydroxypyrrolidin-1-yl | H | 539 |
| 115 | 1-methyl-3-hydroxypiperidin-1-yl | H | 553 |
| 116 | 1-methyl-3-carbamoylpiperidin-1-yl | H | 580 |
| 117 | 1-methyl-4-carbamoylpiperidin-1-yl | H | 580 |
| 118 | 1-methyl-4-fluoropiperidin-1-yl | H | 555 |
| 119 | 1-methyl-4,4-difluoropiperidin-1-yl | H | 573 |
| 120 | 1-methyl-2-(hydroxymethyl)piperidin-1-yl | H | 567 |
| 121 | 4-methyl-3-oxopiperazin-1-yl | H | 552 |
| 122 | 4-methylmorpholin / N-methylpiperazine-morpholine (morpholine with N-methyl linker) | H | 539 |

TABLE 17

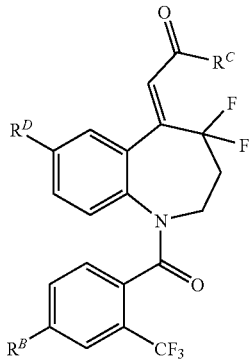

| Ex | $R^B$ | $R^C$ | $R^D$ | MS(+) |
|---|---|---|---|---|
| 123 | —O—(CH$_2$)$_2$CH$_2$F | —NHCH$_2$CH(R—OH)CH$_2$OH | H | 561 |
| 124 | —O—(CH$_2$)$_2$CH$_2$F | —NHCH$_2$CH(S—OH)CH$_2$OH | H | 561 |
| 125 | —O—(CH$_2$)$_2$CH$_2$F | —NH(CH$_2$)$_2$CONH$_2$ | H | 558 |
| 126 | —O—(CH$_2$)$_2$CH$_2$F | 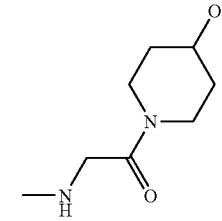 | H | 628 |
| 127 | (S)—O—CH$_2$CHFCH$_3$ | —NH(CH$_2$)$_2$CONH$_2$ | H | 558 |
| 128 | (R)—O—CH$_2$CHFCH$_3$ | —NH(CH$_2$)$_2$CONH$_2$ | H | 558 |
| 129 | (S)—O—CH$_2$CHFCH$_3$ | —NHCH$_2$CH(S—OH)CH$_2$OH | H | 561 |
| 130 | (R)—O—CH$_2$CHFCH$_3$ | —NHCH$_2$CH(S—OH)CH$_2$OH | H | 561 |
| 131 | (S)—O—CH$_2$CHFCH$_3$ | —NHCH$_2$CH(R—OH)CH$_2$OH | H | 561 |
| 132 | (R)—O—CH$_2$CHFCH$_3$ | —NHCH$_2$CH(R—OH)CH$_2$OH | H | 561 |
| 133 | (S)—O—CH$_2$CHFCH$_3$ | —NH(CH$_2$)$_2$CONH$_2$ | F | 576 |
| 134 | (R)—O—CH$_2$CHFCH$_3$ | —NH(CH$_2$)$_2$CONH$_2$ | F | 576 |
| 135 | (S)—O—CH$_2$CHFCH$_3$ | —NHCH$_2$CH(R—OH)CH$_2$OH | F | 579 |
| 136 | (R)—O—CH$_2$CHFCH$_3$ | —NHCH$_2$CH(R—OH)CH$_2$OH | F | 579 |
| 137 | —O—CH$_2$CF$_2$CH$_3$ | —NHCH$_2$CH(R—OH)CH$_2$OH | H | 579 |
| 138 | —O—CH$_2$CF$_2$CH$_3$ | —NHCH$_2$CH(S—OH)CH$_2$OH | H | 579 |
| 139 | —O—CH$_2$CF$_2$CH$_3$ | —NH(CH$_2$)$_2$CONH$_2$ | H | 576 |
| 140 | —O—CH$_2$CF$_2$CH$_3$ | —NH(CH$_2$)$_2$CONH$_2$ | F | 594 |
| 141 | —O—CH$_2$CF$_2$CH$_3$ | —NHCH$_2$CH(S—OH)CH$_2$OH | F | 597 |
| 142 | —O—CH$_2$CF$_2$CH$_3$ | —NHCH$_2$CH(R—OH)CH$_2$OH | F | 597 |
| 143 | —SEt | —NH(CH$_2$)$_2$CONH$_2$ | H | 542 |
| 144 | —SEt | —NHCH(CONH$_2$)$_2$ | H | 571 |
| 145 | —SEt | —NHPh(3-CONH$_2$) | H | 590 |

TABLE 18

| Ex | R14 | MS(+) |
|---|---|---|
| 146 | Gly | 493 |
| 147 | Car | 436 |

In the following, NMR data of some Example compounds are shown in Table 19.

TABLE 19

| Ex | NMR |
|---|---|
| 1 | 2.35-2.55(1H, br), 2.60-2.80(1H, br), 3.00-3.15(1H, br), 3.76(2H, s), 4.75-4.90(1H, br), 5.09(2H, s), 6.45(1H, s), 6.73(1H, d, J=7.8Hz), 6.87(1H, d, J=7.8Hz), 7.03(1H, dd, J=7.8, 2.4Hz), 7.10-7.19(2H, m), 7.24-7.40(9H, m), 8.68(1H, t, J=5.7Hz). |
| 2 | 2.25-2.55(1H, br), 2.60-2.80(1H, br), 3.05-3.20(1H, br), 3.20-3.25(2H, m), 3.42-3.50(2H, m), 4.72(1H, t, J=5.4Hz), 4.75-4.90(1H, br), 5.09(2H, s), 6.39(1H, s), 6.72(1H, d, J=7.8Hz), 6.87(1H, d, J=7.3Hz), 7.04(1H, dd, J=2.0, 8.3Hz), 7.16(1H, t, J=7.6Hz), 7.22-7.42(8H, m), 8.46(1H, t, J=5.4Hz). |
| 3 | 0.24-0.30(2H, m), 0.49-0.58(2H, m), 1.08-1.20(1H, m), 2.33-2.45(1H, br), 2.60-2.97(1H, br), 3.02-3.29(1H, br), 3.68-3.88(4H, m), 4.60-5.05(1H, br), 6.44(1H, s), 6.71(1H, d, J=8.8Hz), 6.85(1H, d, J=8.8Hz), 6.93(1H, dd, J=2.0, 8.8Hz), 7.11-7.38(6H, m), 8.48(1H, t, J=5.4Hz). |
| 4 | 0.24-0.31(2H, m), 0.48-0.56(2H, m), 1.09-1.21(1H, m), 2.27-2.46(1H, br), 2.65-2.90(1H, br), 3.00-3.26(3H, m), 3.43-35.2(2H, m), 3.80(2H, d, J=6.8Hz), 4.73(1H, d, J=5.3Hz), 4.75-4.92(1H, br), 6.39(1H, s), 6.71(1H, d, J=7.3Hz), 6.84(1H, d, J=8.8Hz), 6.93(1H, dd, J=2.5, 8.8Hz), 7.13-7.18(2H, m), 7.24(1H, t, J=7.3Hz) 7.30-7.34(1H, m), 8.48(1H, t, J=5.3Hz). |
| 5 | 0.92(3H, t, J=7.6Hz), 1.46-1.55(2H, m), 2.24-2.50(1H, br), 2.65-2.84(1H, br), 2.89-2.93(2H, m), 3.04-3.22(1H, br), 3.75(2H, s), 4.70-4.92(1H, br), 6.37(1H, s), 6.87(1H, s), 6.94(1H, d, J=7.6Hz), 7.01(1H, d, J=8.0Hz), 7.14-7.53(6H, m), 8.62(1H, s). |
| 6 | 0.93(3H, t, J=7.2Hz), 1.48-1.57(2H, m), 2.28-2.52(1H, br), 2.63-2.87(1H, br), 2.94-2.97(2H, m), 3.08-3.20(1H, br), 3.73-3.76(2H, m), 4.73-4.88(1H, br), 6.48(1H, s), 6.73(1H, d, J=8.0Hz), 6.84(1H, d, J=8.0Hz), 7.14-7.76(7H, m), 8.69(1H, t, J=5.2Hz). |
| 7 | 0.92(3H, t, J=7.3Hz), 1.62-1.72(2H, m), 2.30-2.50(1H, br), 2.60-2.80(1H, br), 3.00-3.10(1H, br), 3.76(2H, s), 3.90(2H, t, J=6.6Hz), 4.70-4.90(1H, br), 6.45(1H, s), 6.72(1H, d, J=7.8Hz), 6.85(1H, d, J=7.8Hz), 6.94(1H, dd, J=2.1, 7.6Hz), 7.10-7.38(6H, m), 8.68(1H, t, J=5.4Hz). |
| 8 | 0.92(3H, t, J=7.3Hz), 1.62-1.72(2H, m), 2.30-2.50(1H, br), 2.60-2.80(1H, br), 3.00-3.20(1H, br), 3.23(2H, t, J=5.9Hz), 3.44-3.50(2H, m), 3.90(2H, t, J=6.6Hz), 4.72(1H, t, J=5.4Hz), 4.75-4.86(1H, br), 6.40(1H, s), 6.71(1H, d, J=7.8Hz), 6.85(1H, d, J=8.3Hz), 6.95(1H, dd, J=2.5, 8.8Hz), 7.10-7.18(2H, m), 7.25(1H, t, J=7.1Hz), 7.30-7.34(1H, m), 8.46(1H, t, J=5.6Hz). |
| 9 | 0.89(3H, t, J=7.3Hz), 1.31-1.42(2H, m), 1.57-1.67(2H, m), 2.30-2.50(1H, br), 2.70-2.85(1H, br), 3.00-3.20(1H, br), 3.76(2H, s), 3.94(2H, t, J=6.6Hz), 4.65-4.95(1H, br), 6.45(1H, s), 6.72(1H, d, J=7.8Hz), 6.85(1H, d, J=8.8Hz), 6.94(1H, dd, J=2.4, 8.8Hz), 7.10-7.20(3H, m), 7.22-7.32(2H, m), 7.33-7.37(1H, m), 8.68(1H, t, J=5.3Hz). |
| 10 | 0.89(3H, t, J=7.4Hz), 1.32-1.42(2H, m), 1.58-1.67(2H, m), 2.25-2.45(1H, br), 2.60-2.80(1H, br), 3.00-3.15(1H, br), 3.20-3.30(2H, m), 3.44-3.50(2H, m), 3.94(2H, t, J=6.4Hz), 4.73(1H, t, J=5.2Hz), 4.75-4.87(1H, br), 6.39(1H, s), 6.71(1H, d, J=7.8Hz), 6.84(1H, d, J=8.8Hz), 6.95(1H, dd, J=2.5, 8.8Hz), 7.12-7.18(2H, m), 7.21-7.26(1H, m), 7.30-7.33(1H, m), 8.46(1H, t, J=5.6Hz). |
| 11 | 0.92(6H, d, J=6.8Hz), 1.89-2.00(1H, m), 2.30-2.50(1H, br), 2.60-2.80(1H, br), 3.00-3.20(1H, br), 3.70-3.82(4H, m), 4.75-4.85(1H, br), 6.45(1H, s), 6.72(1H, d, J=7.9Hz), 6.86(1H, d, J=8.8Hz), 6.95(1H, dd, J=2.4, 8.3Hz), 7.12-7.19(3H, m), 7.23-7.30(2H, m), 7.36(1H, dd, J=7.8Hz, 1.5Hz), 8.68(1H, t, J=5.6Hz). |
| 12 | 0.92(6H, d, J=6.4Hz), 1.89-2.00(1H, m), 2.30-2.50(1H, br), 2.60-2.80(1H, br), 3.00-3.15(1H, br), 3.19-3.25(2H, m), 3.44-3.50(2H, m), 3.72(2H, d, J=6.3Hz), 4.73(1H, t, J=5.1Hz), 4.76-4.88(1H, br), 6.40(1H, s), 6.71(1H, d, J=7.3Hz), 6.85(1H, d, J=8.8Hz), 6.96(1H, dd, J=2.5, 8.3Hz), 7.13-7.18(2H, m), 7.22-7.27(1H, m), 7.32(1H, dd, J=7.8Hz, 1.5Hz), 8.46(1H, t, J=5.6Hz). |

TABLE 19-continued

| Ex | NMR |
|---|---|
| 13 | 0.91(6H, d, J=6.8Hz), 1.86-1.98(1H, m), 2.25-2.50(1H, br), 2.60-2.80(1H, br), 3.00-3.15(1H, br), 3.67(2H, d, J=6.3Hz), 3.70-3.78(2H, br), 4.73-4.90(1H, br), 6.35(1H, s), 6.63-6.69(1H, m), 6.89-6.96(3H, m), 7.11-7.20(2H, m), 7.22-7.33(3H, m), 8.62(1H, s). |
| 14 | 0.80(3H, t, J=7.2Hz), 1.40-1.45(2H, m), 2.27-2.53(1H, br), 2.55-2.77(1H, br), 2.86(3H, s), 2.92-3.15(1H, br), 3.24(2H, s), 3.75(2H, s), 4.71-5.05(1H, br), 6.44(1H, s), 6.58(1H, d, J=8.4Hz), 6.67(1H, d, J=8.4Hz), 6.71(1H, d, J=7.6Hz), 6.77(1H, s), 7.14-7.36(5H, m), 8.64(1H, s). |
| 15 | 2.30-2.50(1H, br), 2.65-2.85(1H, br), 2.80(3H, s), 2.92(3H, s), 3.00-3.20(1H, br), 3.70-3.82(2H, m), 4.75-4.90(1H, br), 4.86(2H, s), 6.44(1H, s), 6.73(1H, d, J=7.8Hz), 6.83(1H, d, J=8.3Hz), 6.90(1H, dd, J=2.4, 8.3Hz), 7.11-7.20(1H, m), 7.24-7.30(2H, m), 7.36(1H, dd, J=7.3Hz, 1.4Hz), 8.68(1H, t, J=5.7Hz). |
| 16 | 0.92(3H, t, J=7.8Hz), 1.61-1.71(2H, m), 2.35-2.55(1H, br), 2.60-2.80(1H, br), 3.00-3.20(1H, br), 3.90(2H, t, J=6.4Hz), 4.70-4.90(1H, br), 6.38(1H, s), 6.72(1H, d, J=7.8Hz), 6.84(1H, d, J=8.7Hz), 6.96(1H, dd, J=2.5, 8.6Hz), 7.10-7.18(2H, m), 7.22-7.27(1H, m), 7.28-7.31(1H, m), 7.35(1H, s), 7.87(1H, s). |
| 17 | 2.30-2.55(1H, br), 2.60-2.80(1H, br), 3.05-3.25(1H, br), 4.75-4.95(1H, br), 5.09(2H, s), 6.38(1H, s), 6.73(1H, d, J=7.8Hz), 6.86(1H, d, J=8.7Hz), 7.05(1H, dd, J=2.4, 8.4Hz), 7.13-7.18(1H, m), 7.22-7.42(9H, m), 7.88(1H, s). |
| 18 | 0.81(3H, t, J=7.2Hz), 1.40-1.46(2H, m), 2.24-2.52(1H, br), 2.57-2.78(1H, br), 2.85(3H, s), 2.95-3.17(1H, br), 3.23(2H, s), 4.70-5.02(1H, br), 6.36(1H, s), 6.62-6.76(4H, m), 7.16-7.34(4H, m), 7.84(1H, s). |
| 19 | 2.30-2.50(1H, br), 2.55-2.80(1H, br), 3.00-3.20(1H, br), 3.75(2H, s), 4.70-4.90(1H, br), 6.47(1H, s), 6.66-6.76(3H, m), 7.00(1H, d, J=1.5Hz), 7.10-7.19(2H, m), 7.22-7.30(2H, m), 7.35(1H, d, J=7.8Hz), 8.65(1H, t, J=5.6Hz), 10.3(1H, s). |
| 20 | 2.30-2.50(1H, br), 2.55-2.80(1H, br), 3.00-3.20(1H, br), 4.70-4.90(1H, br), 6.41(1H, s), 6.67-6.74(3H, m), 7.00(1H, s), 7.15(1H, tdJ=1.4, 7.8Hz), 7.24(1H, t, J=7.6Hz), 7.27-7.32(1H, m), 7.34(1H, s), 7.85(1H, s), 10.3(1H, s). |
| 21 | 0.87(3H, t, J=7.2Hz), 1.19-1.27(1H, m), 1.45-1.58(1H, m), 2.18-2.52(1H, br), 2.65-2.78(1H, br), 2.93-3.00(2H, m), 3.06-3.25(1H, br), 3.74-3.76(2H, m), 4.75-4.92(1H, br), 6.55(1H, s), 6.73(1H, d, J=7.6Hz), 7.12-7.15(3H, m), 7.24-7.33(2H, m), 7.36(1H, dd, J=1.6, 7.2Hz), 7.71(1H, d, J=8.0Hz), 7.98(1H, s), 8.70(1H, s). |
| 22 | 0.84(3H, t, J=7.6Hz), 1.38-1.47(2H, m), 2.15-2.54(1H, br), 2.67-2.90(1H, br), 3.15-3.30(1H, br), 3.34-3.52(2H, m), 3.75-3.77(2H, m), 4.75-4.90(1H, br), 6.61(1H, s), 6.74(1H, d, J=8.0Hz), 7.13-7.17(3H, m), 7.26-7.39(2H, m), 7.37-7.39(1H, m), 7.97(1H, d, J=8.4Hz), 8.16(1H, s), 8.71(1H, s). |
| 30 | 1.32(3H, dd, J=6.4, 29.2Hz), 2.31-2.43(1H, br), 2.60-2.80(1H, br), 3.18-3.27(1H, br), 3.20-3.34(2H, m), 4.00-4.37(2H, m), 4.64-5.10(2H, m), 6.56(1H, s), 6.73-6.80(1H, m), 6.87(1H, d, J=8.8Hz), 7.02-7.08(2H, m), 7.14(1H, s), 7.24-7.26(2H, m), 7.32(1H, s), 8.60-8.64(1H, br). |
| 31 | 1.33(3H, ddJ=6.3, 29.3Hz), 2.33-2.47(1H, br), 2.59-2.83(1H, br), 3.03-3.25(1H, br), 3.72-3.85(2H, m), 4.02-4.24(2H, m), 4.72-4.84(1H, br), 4.86-5.07(1H, br), 6.56(1H, s), 6.74-6.80(1H, m), 6.88(1H, d, J=8.8Hz), 7.00-7.08(2H, m), 7.14(1H, s), 7.21-7.26(2H, m), 7.32(1H, s), 8.65(1H, t, J=5.4Hz). |
| 51 | 1.67(3H, t, J=19.5Hz), 2.30-2.48(1H, br), 2.46-2.90(1H, br), 3.08-3.34(3H, m), 3.39-4.00(2H, m), 4.32(2H, t, J=12.7Hz), 4.70-4.78(2H, m), 6.38(1H, s), 6.72(1H, d, J=7.8Hz), 6.89(1H, d, J=8.8Hz), 7.04(1H, dd, J=2.4, 8.8Hz), 7.15(1H, dt, J=1.5, 7.8Hz), 7.22-7.34(3H, m), 8.47(1H, t, J=5.3Hz). |
| 52 | 1.32(3H, dd, J=6.4, 23.5Hz), 2.36-2.47(1H, br), 2.65-2.76(1H, br), 3.18-3.30(3H, m), 3.43-3.49(2H, m), 4.00-4.20(2H, m), 4.68-5.06(3H, m), 6.39(1H, s), 6.72(1H, d, J=8.8Hz), 6.87(1H, d, J=8.8Hz), 6.98(1H, dd, J=2.4, 8.8Hz), 7.15(1H, dt, J=1.4, 8.8Hz), 7.21-7.27(2H, m), 7.32(1H, dd, J=1.4, 8.8Hz), 8.46(1H, t, J=5.8Hz). |
| 53 | 1.32(3H, dd, J=6.8, 23.9Hz), 2.37-2.46(1H, br), 2.65-2.83(1H, br), 3.19-3.28(3H, m), 3.44-3.50(2H, m), 4.00-4.20(2H, m), 4.69-5.05(3H, m), 6.39(1H, s), 6.73(1H, d, J=8.8Hz), 6.87(1H, d, J=8.8Hz), 6.99(1H, dd, J=2.4, 8.8Hz), 7.15(1H, dt, J=1.4, 8.8Hz), 7.21-7.27(2H, m), 7.32(1H, dd, J=1.4, 8.8Hz), 8.46(1H, t, J=5.4Hz). |
| 54 | 1.33(3H, dd, J=5.9, 29.8Hz), 2.31-2.46(1H, br), 2.61-2.84(1H, br), 3.18-3.26(2H, m), 3.44-3.50(2H, m) 4.01-4.22(2H, m), 4.74(1H, t, J=5.3Hz), 4.76-4.85(1H, br), 4.96-5.06(1H, m), 6.51(1H, s), 6.70-6.77(1H, m)6.86(1H, d, J=8.8Hz), 7.01-7.08(1H, m), 7.19(2H, dd, J=2.9, 8.8Hz), 7.25(1H, d, J=2.9Hz), 7.66(1H, d, J=8.8Hz), 8.46(1H, t, J=5.9Hz). |
| 55 | 1.32(3H, dd, J=5.9, 29.8Hz), 2.32-2.46(1H, br), 2.61-2.84(1H, br), 3.03-3.27(2H, m), 3.44-3.51(2H, m), 4.02-4.22(2H, m), 4.74(1H, t, J=5.3Hz), 4.76-4.85(1H, br), 4.87-5.06(1H, m), 6.52(1H, s), 6.70-6.78(1H, m), 6.87(1H, d, J=8.8Hz), 7.00-7.08(1H, m), 7.19(2H, dd, J=2.9, 8.8Hz), 7.24(1H, d, J=2.9Hz), 7.67(1H, d, J=8.8Hz), 8.47(1H, t, J=5.4Hz). |
| 56 | 1.69(3H, t, J=19.6Hz), 2.31-2.46(1H, br), 2.61-2.83(1H, br), 3.05-3.27(3H, m), 3.43-3.50(2H, m), 4.34(2H, t, J=12.7Hz), 4.68-4.86(2H, m), 6.50(1H, s), 6.73-6.78(1H, m), 6.89(1H, d, J=8.8Hz), 7.01-7.13(1H, m), 7.20(1H, dd, J=2.9, 8.8Hz), 7.31(1H, d, J=2.9Hz), 8.43(1H, t, J=5.4Hz). |
| 84 | 0.97(3H, t, J=7.3Hz), 1.61-1.72(2H, m), 2.31-2.47(1H, br), 2.65-2.81(1H, br), 2.99-3.17(1H, m), 3.32-3.40(2H, m), 3.52-3.61(1H, m), 3.90(2H, t, J=7.3Hz), 4.54(1H, t, J=5.9Hz), 4.75-4.87(2H, m), 6.40(1H, s), 6.71(1H, d, J=8.8Hz), 6.85(1H, d, J=8.8Hz), 6.95(1H, dd, J=2.5, 8.8Hz), 7.12-7.19(2H, m), 7.24(1H, t, J=8.8Hz), 7.34(1H, dd, J=1.4, 8.8Hz), 8.45(1H, t, J=5.4Hz). |
| 85 | 0.98(3H, t, J=7.3Hz), 1.61-1.71(2H, m), 2.30-2.46(1H, br), 2.65-2.80(1H, br), 2.99-3.20(3H, m), 3.32-3.39(2H, m), 3.51-3.62(1H, m), 3.90(2H, t, J=7.3Hz), 4.54(1H, t, J=5.9Hz), 4.76-4.90(2H, m), 6.40(1H, s), 6.71(1H, d, J=8.8Hz), 6.86(1H, d, J=8.8Hz), 6.94(1H, dd, J=2.5, 8.8Hz), 7.12-7.19(2H, m), 7.24(1H, t, J=8.8Hz), 7.34(1H, dd, J=1.4, 8.8Hz), 8.45(1H, t, J=5.4Hz). |
| 86 | 0.93(3H, t, J=6.8Hz), 1.61-1.72(2H, m), 2.31-2.46(1H, br), 2.61-2.83(1H, br), 3.00-3.21(3H, m), 3.31-3.39(2H, m), 3.52-3.63(1H, m), 3.92(2H, t, J=6.8Hz), 4.56(1H, t, J=5.9Hz), 4.52-4.86(2H, m), 6.53(1H, s), 6.71-6.77(1H, m), 6.85(1H, d, J=8.8Hz), 6.99(1H, dd, J=2.0, 8.8Hz), 7.04(1H, dt, J=2.0, 8.8Hz), 7.17(1H, d, J=2.0Hz), 7.21(1H, dd, J=2.0, 8.8Hz), 8.42(1H, t, J=5.3Hz). |
| 129 | 1.32(3H, dd, J=6.3, 23.4Hz), 2.34-2.46(1H, br), 2.55-2.83(1H, br), 3.20-3.32(3H, m), 3.35-3.40(2H, m), 3.52-3.60(1H, m), 4.00-4.20(2H, m), 4.50-4.59(1H, m), 4.73-5.05(3H, m), 6.39(1H, s), 6.72(1H, d, J=8.8Hz), 6.87(1H, d, J=8.8Hz), 6.98(1H, dd, J=2.5, 8.8Hz), 7.15(1H, dt, J=2.5, 8.8Hz), 7.19-7.27(2H, m), 7.34(1H, dd, J=1.4, 8.8Hz), 8.47(1H, t, J=5.4Hz). |

TABLE 19-continued

| Ex | NMR |
|---|---|
| 130 | 1.31(3H, dd, J=6.3, 23.4Hz), 2.26-2.47(1H, br), 2.62-2.84(1H, br), 3.00-3.23(3H, m), 3.32-3.38(2H, m), 3.53-3.62(1H, m), 4.00-4.20(2H, m), 4.45(1H, t, J=5.4Hz), 4.76-5.05(3H, m), 6.40(1H, s), 6.72(1H, d, J=7.8Hz), 6.88(1H, d, J=8.8Hz), 6.99(1H, dd, J=2.5, 8.8Hz), 7.15(1H, dt, J=1.4, 7.8Hz), 7.20-7.28(2H, m), 7.34(1H, dd, J=1.4, 7.8Hz), 8.47(1H, t, J=5.9Hz). |
| 132 | 1.31(3H, dd, J=6.4, 23.4Hz), 2.30-2.46(1H, br), 2.54-2.80(1H, br), 3.00-3.32(3H, m), 3.34-3.40(2H, m), 3.52-3.61(1H, m), 4.00-4.20(2H, m), 4.51-4.60(1H, m), 4.72-5.05(3H, m), 6.40(1H, s), 6.72(1H, d, J=8.8Hz), 6.87(1H, d, J=8.8Hz), 6.99(1H, dd, J=2.5, 8.8Hz), 7.15(1H, dd, J=2.5, 8.8Hz), 7.19-7.29(2H, m), 7.31-7.36(1H, m), 8.46(1H, t, J=5.4Hz). |
| 133 | 1.33(3H, dd, J=6.3, 23.9Hz), 2.27-2.46(3H, m), 2.60-2.84(1H, br), 3.22-3.34(1H, br), 3.34-3.40(2H, m), 4.00-4.22(2H, m), 4.70-5.06(2H, m), 6.44(1H, s), 6.71-6.76(1H, m), 6.81-6.89(2H, m), 7.01-7.07(2H, m), 7.19(1H, dd, J=2.9, 8.8Hz), 7.24(1H, d, J=2.9Hz), 7.33-7.38(1H, br), 8.45-8.52(1H, br). |
| 134 | 1.33(3H, dd, J=6.4, 29.8Hz), 2.26-2.46(3H, m), 2.64-2.87(1H, br), 3.00-3.23(1H, br), 3.27-3.42(2H, m), 4.01-4.22(2H, m), 4.66-5.07(2H, m), 6.49(1H, s), 6.71-6.78(1H, m), 6.87(2H, d, J=8.8Hz), 7.00-7.08(2H, m), 7.19(1H, dd, J=2.9, 8.8Hz), 7.24(1H, d, J=2.9Hz), 7.33-7.39(1H, m), 8.50(1H, t, J=5.4Hz). |
| 135 | 1.32(3H, dd, J=6.3, 23.9Hz), 2.32-2.46(1H, br), 2.63-2.84(1H, br), 3.00-3.24(3H, m), 3.33-3.40(2H, m), 3.52-3.61(1H, m), 4.01-4.21(2H, m), 4.57(1H, t, J=5.3Hz), 4.73-5.06(3H, m), 6.52-1H, s), 6.72-6.78(1H, m), 6.87(1H, d, J=8.8Hz), 7.00-7.08(2H, m), 7.18-7.26(2H, m), 8.38-8.48(1H, m). |
| 136 | 1.33(3H, dd, J=6.3, 13.4Hz), 2.34-2.47(1H, br), 2.56-2.82(1H, br), 3.01-3.32(3H, m), 3.33-3.39(2H, m), 3.52-3.61(1H, m), 4.02-4.22(2H, m), 4.57(1H, t, J=5.4Hz), 4.75-4.85(2H, m), 4.87-5.07(1H, m), 6.51(1H, s), 6.71-6.77(1H, m), 6.87(1H, d, J=8.3Hz), 7.01-7.08(2H, m), 7.19-7.25(2H, m), 8.43(1H, t, J=5.4Hz). |
| 140 | 1.69(3H, t, J=19.3Hz), 2.26-2.47(3H, m)2.62-2.83(1H, br), 3.05-3.22(1H, br), 3.25-3.44(2H, m), 4.34(2H, t, J=12.4Hz), 4.68-4.92(1H, br), 6.48(1H, s), 6.72-6.77(1H, m), 6.83-6.95(2H, m), 7.01-7.13(2H, m), 7.19(1H, dd, J=2.9, 8.8Hz), 7.30(1H, d, J=2.9Hz), 7.34-7.40(1H, br), 8.50(1H, t, J=5.3Hz). |

In the following, structures of other compounds of the invention are shown in Tables 20 to 36. These are synthesized or can be synthesized by using the aforementioned production methods or the methods described in Examples, or methods obvious to those skilled in the art or modified methods thereof.

In this connection, signs in the tables represent the following meanings.

No: compound number.

$R^{1A}$, -$A^A$-$B^A$, X, Y: substituent groups in respective general formulae, iPr: isopropyl, tBu: tert-butyl, cBu: cyclobutyl, nPen: normal pentyl, cPen: cyclopentyl, iAm: isoamyl, nHex: normal hexyl, pyrr: pyrrolidin-1-yl, pipe: piperidin-1-yl, pipa: piperazin-1-yl, mor: morpholin-4-yl, Ac: acetyl, Ms: methanesulfonyl, cyano: cyano.

TABLE 20

| No | $R^{1A}$ | —$A^A$-$B^A$ |
|---|---|---|
| A1 | Gly | —O-Me |
| A2 | Gly | —O-Et |
| A3 | Etha | —O-Et |
| A4 | Car | —O-Et |
| A5 | Etha | —O-iPr |

TABLE 20-continued

| No | $R^{1A}$ | —$A^A$-$B^A$ |
|---|---|---|
| A6 | Car | —O-nBu |
| A7 | Car | —O-iBu |
| A8 | Gly | —O-tBu |
| A9 | Gly | —O-iAm |
| A10 | Gly | —O-nPen |
| A11 | Etha | —O-nHex |
| A12 | Gly | —O-cPen |
| A13 | Gly | —O—Ph |
| A14 | Car | —O—Ph |
| A15 | Gly | —O—CH$_2$CF$_3$ |
| A16 | Gly | —O—CH$_2$CHF$_2$ |
| A17 | Gly | —O—CH$_2$CH=CH |
| A18 | Gly | —O—(CH$_2$)$_2$CH≡CH |
| A19 | Gly | —O—(CH$_2$)$_2$OMe |
| A20 | Car | —O—CH$_2$cPr |
| A21 | Gly | —O—CH$_2$cBu |
| A22 | Car | —O—CH$_2$cBu |
| A23 | Gly | —O—CH$_2$tBu |
| A24 | Etha | —O—CH$_2$tBu |
| A25 | Gly | —O—CH$_2$CONH$_2$ |
| A27 | Gly | —O—CH$_2$CONHMe |
| A28 | Gly | —O—(CH$_2$)$_2$-cyano |
| A29 | Etha | —O—(CH$_2$)$_2$-cyano |
| A30 | Car | —O—(CH$_2$)$_2$-cyano |
| A31 | Etha | —O—CH$_2$CH(Me)OMe |
| A32 | Etha | —O—CH$_2$CH(Me)OMe |
| A33 | Car | —O—CH$_2$CH(Me)OMe |

TABLE 20-continued

| No | R^14 | —A^A-B^A |
|---|---|---|
| A34 | Etha | —O—CH₂CF₂CF₃ |
| A35 | Car | —O—CH₂CF₂CF₃ |
| A36 | Etha | —O—CH₂CF₂CHF₂ |
| A37 | Car | —O—CH₂CF₂CHF₂ |
| A38 | Gly | —O—(CH₂)₂OH |
| A39 | Etha | —O—(CH₂)₂OH |
| A40 | Car | —O—(CH₂)₂OH |
| A41 | Gly | —O—CH₂CO₂H |
| A42 | Etha | —O—CH₂CO₂H |
| A43 | Car | —O—CH₂CO₂H |
| A44 | Etha | —N(Me)-iBu |
| A45 | Car | —N(Me)-iBu |
| A46 | Etha | —S-Et |
| A47 | Car | —S-Et |
| A48 | Gly | —S-iPr |
| A49 | Etha | —S-iPr |
| A50 | Car | —S-iPr |
| A51 | Gly | —N(Me)—CH₂CH₂OMe |
| A52 | Etha | —N(Me)—CH₂CH₂OMe |
| A53 | Car | —N(Me)—CH₂CH₂OMe |
| A55 | Gly | —N(Me)-nBu |
| A56 | Etha | —N(Me)-nBu |
| A57 | Car | —N(Me)-nBu |
| A58 | Etha | —N(nPr)-nPr |

TABLE 21

| No | R^14 | —A^A-B^A |
|---|---|---|
| A59 | —NHCH₂CH(S—OH)CH₂OH | (S)—O—CH₂CHFCH₃ |
| A60 | —NHCH₂CH(S—OH)CH₂OH | (R)—O—CH₂CHFCH₃ |

TABLE 22

| No | R^14 | —A^A-B^A |
|---|---|---|
| A61 | Gly | —O-Et |
| A62 | Car | —O-nPr |
| A63 | Gly | —O-iPr |
| A64 | Etha | —O-nBu |

TABLE 23

| No | R^14 | —X— | Y | —A^A-B^A |
|---|---|---|---|---|
| B1 | Gly | —N=C— | N | —O-nPr |
| B2 | Etha | —N=C— | N | —O-nPr |
| B3 | Car | —N=C— | N | —O-nPr |
| B4 | Gly | —N=C— | N | —O-iBu |
| B5 | Etha | —N=C— | N | —O-iBu |
| B6 | Car | —N=C— | N | —O-iBu |
| B7 | Gly | —N=C— | N | —S-nPr |
| B8 | Etha | —N=C— | N | —S-nPr |
| B9 | Car | —N=C— | N | —S-nPr |
| B10 | Gly | —N=C— | N | —N(Me)-nPr |
| B11 | Etha | —N=C— | N | —N(Me)-nPr |
| B12 | Car | —N=C— | N | —N(Me)-nPr |
| B13 | Gly | —N=N— | CH | —O-nPr |
| B14 | Etha | —N=N— | CH | —O-nPr |
| B15 | Car | —N=N— | CH | —O-nPr |
| B16 | Gly | —N=N— | CH | —O-iBu |
| B17 | Etha | —N=N— | CH | —O-iBu |
| B18 | Car | —N=N— | CH | —O-iBu |
| B19 | Gly | —N=N— | CH | —S-nPr |
| B20 | Etha | —N=N— | CH | —S-nPr |
| B21 | Car | —N=N— | CH | —S-nPr |
| B22 | Gly | —N=N— | CH | —N(Me)-nPr |
| B23 | Etha | —N=N— | CH | —N(Me)-nPr |
| B24 | Car | —N=N— | CH | —N(Me)-nPr |
| B25 | Gly | —S— | N | —O-nPr |
| B26 | Etha | —S— | N | —O-nPr |
| B27 | Car | —S— | N | —O-nPr |
| B28 | Gly | —S— | N | —O-iBu |
| B29 | Etha | —S— | N | —O-iBu |

TABLE 23-continued

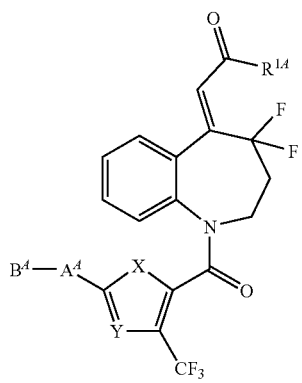

| No | R^{1A} | —X— | Y | —A^A-B^A |
|---|---|---|---|---|
| B30 | Car | —S— | N | —O-iBu |
| B31 | Gly | —S— | N | —S-nPr |
| B32 | Etha | —S— | N | —S-nPr |
| B33 | Car | —S— | N | —S-nPr |
| B34 | Gly | —S— | N | —N(Me)-nPr |
| B35 | Etha | —S— | N | —N(Me)-nPr |

TABLE 24

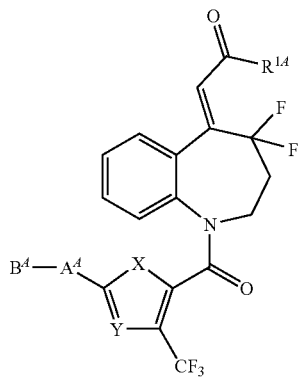

| No | R^{1A} | —X— | Y | —A^A-B^A |
|---|---|---|---|---|
| B36 | Car | —S— | N | —N(Me)-nPr |
| B37 | Gly | —N=C— | CH | —O-nPr |
| B38 | Etha | —N=C— | CH | —O-nPr |
| B39 | Car | —N=C— | CH | —O-nPr |
| B40 | Gly | —N=C— | CH | —O-iBu |
| B41 | Etha | —N=C— | CH | —O-iBu |
| B42 | Car | —N=C— | CH | —O-iBu |
| B43 | Gly | —N=C— | CH | —S-nPr |
| B44 | Etha | —N=C— | CH | —S-nPr |
| B45 | Car | —N=C— | CH | —S-nPr |
| B46 | Gly | —N=C— | CH | —N(Me)-nPr |
| B47 | Etha | —N=C— | CH | —N(Me)-nPr |
| B48 | Car | —N=C— | CH | —N(Me)-nPr |

TABLE 25

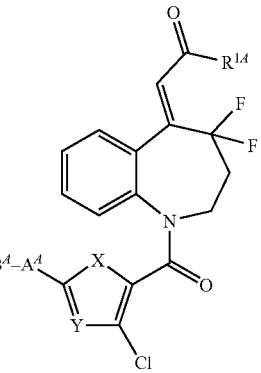

| No | R^{1A} | —X— | Y | —A^A-B^A |
|---|---|---|---|---|
| B49 | Etha | —C=C— | N | —O-nPr |
| B50 | Gly | —C=C— | N | —O-iBu |
| B51 | Etha | —C=C— | N | —O-iBu |
| B52 | Car | —C=C— | N | —O-iBu |
| B53 | Gly | —C=C— | N | —S-nPr |
| B54 | Etha | —C=C— | N | —S-nPr |
| B55 | Car | —C=C— | N | —S-nPr |
| B56 | Gly | —C=C— | N | —N(Me)-nPr |
| B57 | Etha | —C=C— | N | —N(Me)-nPr |
| B58 | Car | —C=C— | N | —N(Me)-nPr |
| B59 | Gly | —S— | CH | —O-nPr |
| B60 | Etha | —S— | CH | —O-nPr |
| B61 | Car | —S— | CH | —O-nPr |
| B62 | Gly | —S— | CH | —O-iBu |
| B63 | Etha | —S— | CH | —O-iBu |
| B64 | Car | —S— | CH | —O-iBu |
| B65 | Gly | —S— | CH | —S-nPr |
| B66 | Etha | —S— | CH | —S-nPr |
| B67 | Car | —S— | CH | —S-nPr |

TABLE 26

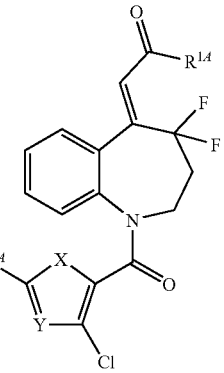

| No | R^{1A} | X | Y | —A^A-B^A |
|---|---|---|---|---|
| B68 | Gly | N | S | —N(Me)-nPr |
| B69 | Etha | N | S | —N(Me)-nPr |
| B70 | Car | N | S | —N(Me)-nPr |

TABLE 27

| No | R$^{1A}$ | —A$^A$-B$^A$ |
|---|---|---|
| C1 | Gly | —O-iBu |
| C2 | Etha | —O-iBu |
| C3 | Car | —O-iBu |
| C4 | Gly | —O-nBu |
| C5 | Etha | —O-nBu |
| C6 | Car | —O-nBu |
| C7 | Gly | —S-nPr |
| C8 | Etha | —S-nPr |
| C9 | Car | —S-nPr |
| C10 | Gly | —S-iPr |
| C11 | Etha | —S-iPr |
| C12 | Car | —S-iPr |
| C13 | Gly | —S-Et |
| C14 | Etha | —S-Et |
| C15 | Car | —S-Et |
| C16 | Gly | —N(Me)-nPr |
| C17 | Etha | —N(Me)-nPr |
| C18 | Car | —N(Me)-nPr |

TABLE 28

| No | R$^{1A}$ | —A$^A$-B$^A$ |
|---|---|---|
| C19 | Gly | —O-nPr |
| C20 | Etha | —O-nPr |
| C21 | Car | —O-nPr |
| C22 | Gly | —O-iBu |
| C23 | Etha | —O-iBu |
| C24 | Car | —O-iBu |
| C25 | Gly | —O-nBu |
| C26 | Etha | —O-nBu |
| C27 | Car | —O-nBu |
| C28 | Gly | —S-nPr |
| C29 | Etha | —S-nPr |
| C30 | Car | —S-nPr |
| C31 | Gly | —S-iPr |
| C32 | Etha | —S-iPr |
| C33 | Car | —S-iPr |

TABLE 28-continued

| No | R$^{1A}$ | —A$^A$-B$^A$ |
|---|---|---|
| C34 | Gly | —S-Et |
| C35 | Etha | —S-Et |
| C36 | Car | —S-Et |
| C37 | Gly | —N(Me)-nPr |
| C38 | Etha | —N(Me)-nPr |
| C39 | Car | —N(Me)-nPr |

TABLE 29

| No | R$^{1A}$ | —A$^A$-B$^A$ |
|---|---|---|
| C40 | Gly | —O-iBu |
| C41 | Etha | —O-iBu |
| C42 | Car | —O-iBu |
| C43 | Gly | —O-nBu |
| C44 | Etha | —O-nBu |
| C45 | Car | —O-nBu |
| C46 | Gly | —S-nPr |
| C47 | Etha | —S-nPr |
| C48 | Car | —S-nPr |
| C49 | Gly | —S-iPr |
| C50 | Etha | —S-iPr |
| C51 | Car | —S-iPr |
| C54 | Gly | —S-Et |
| C55 | Etha | —S-Et |
| C56 | Car | —S-Et |
| C57 | Gly | —N(Me)-nPr |
| C58 | Etha | —N(Me)-nPr |
| C59 | Car | —N(Me)-nPr |

TABLE 30

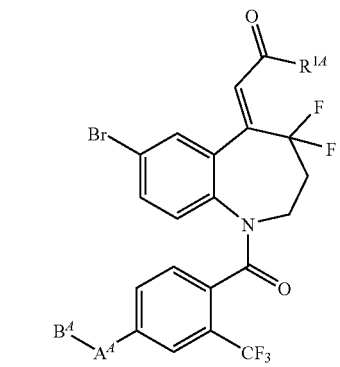

| No | $R^{1A}$ | —$A^A$-$B^A$ |
|---|---|---|
| C60 | Etha | —O-nPr |
| C61 | Gly | —O-iBu |
| C62 | Etha | —O-iBu |
| C63 | Car | —O-iBu |
| C64 | Gly | —O-nBu |
| C65 | Etha | —O-nBu |
| C66 | Car | —O-nBu |
| C67 | Gly | —S-nPr |
| C68 | Etha | —S-nPr |
| C69 | Car | —S-nPr |
| C70 | Gly | —S-iPr |
| C71 | Etha | —S-iPr |
| C72 | Car | —S-iPr |
| C73 | Gly | —S-Et |
| C74 | Etha | —S-Et |
| C75 | Car | —S-Et |
| C76 | Gly | —N(Me)-nPr |
| C77 | Etha | —N(Me)-nPr |
| C78 | Car | —N(Me)-nPr |

TABLE 31

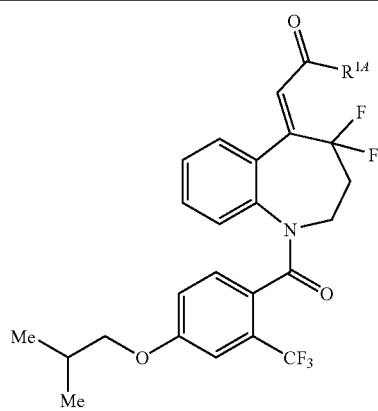

| No | $R^{1A}$ |
|---|---|
| D1 | $NHCH_2$-(2-Py) |
| D2 | NHPh |
| D3 | $NHCH_2Ph$ |
| D4 | $NHCH_2$-(2-HO—Ph) |
| D5 | $NHCH_2$-(3-HO—Ph) |
| D6 | $NHCH_2$-(4-HO—Ph) |
| D7 | $NHCH_2$-(2-$H_2$NOC—Ph) |
| D8 | $NHCH_2$-(3-$H_2$NOC—Ph) |
| D9 | $NHCH_2$-(4-$H_2$NOC—Ph) |
| D10 | NH-(2-HO—Ph) |
| D11 | NH-(3-HO—Ph) |
| D12 | NH-(4-HO—Ph) |
| D13 | NH-(2-$H_2$NOC—Ph) |
| D14 | NH-(3-$H_2$NOC—Ph) |
| D15 | NH-(4-$H_2$NOC—Ph) |
| D16 | NH-$(CH_2)_2$OMe |
| D17 | NH-$(CH_2)_3$OH |
| D18 | $N(CH_2CH_2OH)_2$ |
| D19 | $NHCH_2CH(CH_2OH)OH$ |
| D20 | $N(Me)CH_2CH_2OH$ |
| D21 | 3-HO-pyrr |
| D22 | 3-HO-pipe |
| D23 | 4-HO-pipe |
| D24 | $NHCH_2CONHMe$ |
| D25 | $NHCH_2CONMe_2$ |
| D26 | $N(Me)CH_2CONH_2$ |
| D27 | $N(Me)CH_2CONHMe$ |
| D28 | $N(Me)CH_2CONMe_2$ |
| D29 | $NH(CH_2)_2CONH_2$ |
| D30 | $N(CH_2CONH_2)_2$ |
| D31 | $NHCH(CONH_2)CH_2OH$ |
| D32 | 3-$H_2$NOC-pipe |
| D33 | 4-$H_2$NOC-pipe |
| D34 | $NHCH_2CO$-pyrr |
| D35 | $NHCH_2CO$-(3-HO-pyrr) |
| D36 | $NHCH_2CO$-(3-HO-pipe) |
| D37 | $NHCH_2CO$-(4-HO-pipe) |
| D38 | NH-(3-Ac—Ph) |
| D39 | NH-(3-MeHNOC—Ph) |
| D40 | $NHCH_2$-(4-$H_2NO_2$S—Ph) |
| D41 | NH-(3-Ms—Ph) |
| D42 | $NHCH_2CO$-mor |
| D43 | $NHCH_2$-(6-HO-2-Py) |
| D44 | $NHCH_2$-(6-MeO-2-Py) |
| D45 | $NHCH_2$-(6-$H_2$NOC-2-Py) |
| D46 | $NHCH_2$-(6-cyano-2-Py) |
| D47 | $NHCH_2$-(6-$Me_2$NOC-2-Py) |
| D48 | $NHCH_2$-(6-$H_2$N-2-Py) |
| D49 | $NHCH_2$-(6-$Me_2$N-2-Py) |
| D50 | $NHCH_2$-(6-F-2-Py) |
| D51 | $NHCH_2$-(6-Cl-2-Py) |
| D52 | $NHCH_2$-(6-Me-2-Py) |
| D53 | $NHCH_2$-(pyrazol-2-yl) |
| D54 | $NHCH_2$-(pyridazine-2-yl) |
| D55 | $NHCH_2$-(pyrimidine-2-yl) |
| D56 | $N(CH_2CONH_2)((CH_2)_2OH)$ |
| D57 | $NHCH(Me)CH_2OH$ |
| D58 | $NHCH_2CH(Me)OH$ |
| D59 | $NHC(Me)_2CH_2OH$ |
| D60 | $NHCH_2C(Me)_2OH$ |
| D61 | 3-oxo-pipa |
| D62 | $NHCH_2CO$-(3-$H_2$NOC-pipe) |
| D63 | $NHCH_2CO$-(4-$H_2$NOC-pipe) |
| D64 | $NHCH(CH_2OH)_2$ |

TABLE 32

| No | $R^{1A}$ |
|---|---|
| E1 | NHCH$_2$Ph |
| E2 | NHCH$_2$-(2-HO—Ph) |
| E3 | NHCH$_2$-(2-H$_2$NOC—Ph) |
| E4 | NHCH$_2$-(3-H$_2$NOC—Ph) |
| E5 | NHCH$_2$-(4-H$_2$NOC—Ph) |
| E6 | N(Me)CH$_2$CH$_2$OH |
| E7 | 4-HO-pipe |
| E8 | N(Me)CH$_2$CONH$_2$ |
| E9 | N(Me)CH$_2$CONHMe |
| E10 | N(Me)CH$_2$CONMe$_2$ |
| E11 | NHCH(CONH$_2$)CH$_2$OH |
| E12 | NHCH$_2$CO-(3-HO-pipe) |
| E13 | NH-(3-Ac—Ph) |
| E14 | NH-(3-MeHNOC—Ph) |
| E15 | NHCH$_2$-(4-H$_2$NO$_2$S—Ph) |
| E16 | NH-(3-Ms—Ph) |
| E17 | NHCH$_2$CO-mor |
| E18 | NHCH$_2$-(6-HO-2-Py) |
| E19 | NHCH$_2$-(6-MeO-2-Py) |
| E20 | NHCH$_2$-(6-H$_2$NOC-2-Py) |
| E21 | NHCH$_2$-(6-cyano-2-Py) |
| E22 | NHCH$_2$-(6-Me$_2$NOC-2-Py) |
| E23 | NHCH$_2$-(6-H$_2$N-2-Py) |
| E24 | NHCH$_2$-(6-Me$_2$N-2-Py) |
| E25 | NHCH$_2$-(6-F-2-Py) |
| E26 | NHCH$_2$-(6-Cl-2-Py) |
| E27 | NHCH$_2$-(6-Me-2-Py) |
| E28 | NHCH$_2$-(pyrazol-2-yl) |
| E29 | NHCH$_2$-(pyridazine-2-yl) |
| E30 | NHCH$_2$-(pyrimidine-2-yl) |
| E31 | N(CH$_2$CONH$_2$)((CH$_2$)$_2$OH) |
| E32 | NHCH(Me)CH$_2$OH |
| E33 | NHCH$_2$CH(Me)OH |
| E34 | NHCH$_2$C(Me)$_2$OH |
| E35 | NHCH$_2$CO-(3-H$_2$NOC-pipe) |
| E36 | NHCH$_2$CO-(4-H$_2$NOC-pipe) |
| E37 | NHCH(CH$_2$OH)$_2$ |

TABLE 33

| No | $R^{1A}$ |
|---|---|
| F1 | NHCH$_2$-(2-Py) |
| F2 | NHPh |
| F3 | NHCH$_2$Ph |
| F4 | NHCH$_2$-(2-HO—Ph) |
| F5 | NHCH$_2$-(3-HO—Ph) |
| F6 | NHCH$_2$-(4-HO—Ph) |
| F7 | NHCH$_2$-(2-H$_2$NOC—Ph) |
| F8 | NHCH$_2$-(3-H$_2$NOC—Ph) |
| F9 | NHCH$_2$-(4-H$_2$NOC—Ph) |
| F10 | NH-(2-HO—Ph) |
| F11 | NH-(3-HO—Ph) |
| F12 | NH-(4-HO—Ph) |
| F13 | NH-(2-H$_2$NOC—Ph) |
| F14 | NH-(3-H$_2$NOC—Ph) |
| F15 | NH-(F-H$_2$NOC—Ph) |
| F16 | NH-(CH$_2$)$_2$OMe |
| F17 | NH-(CH$_2$)$_3$OH |
| F18 | N(CH$_2$CH$_2$OH)$_2$ |
| F19 | NHCH$_2$CH(CH$_2$OH)OH |
| F20 | N(Me)CH$_2$CH$_2$OH |
| F21 | 3-HO-pyrr |
| F22 | 3-HO-pipe |
| F23 | 4-HO-pipe |
| F24 | NHCH$_2$CONHMe |
| F25 | NHCH$_2$CONMe$_2$ |
| F26 | N(Me)CH$_2$CONH$_2$ |
| F27 | N(Me)CH$_2$CONHMe |
| F28 | N(Me)CH$_2$CONMe$_2$ |
| F29 | NH(CH$_2$)$_2$CONH$_2$ |
| F30 | N(CH$_2$CONH$_2$)$_2$ |
| F31 | NHCH(CONH$_2$)CH$_2$OH |
| F32 | 3-H$_2$NOC-pipe |
| F33 | 4-H$_2$NOC-pipe |
| F34 | NHCH$_2$CO-pyrr |
| F35 | NHCH$_2$CO-(3-HO-pyrr) |
| F36 | NHCH$_2$CO-(3-HO-pipe) |
| F37 | NHCH$_2$CO-(4-HO-pipe) |
| F38 | NH-(3-Ac—Ph) |
| F39 | NH-(3-MeHNOC—Ph) |
| F40 | NHCH$_2$-(4-H$_2$NO$_2$S—Ph) |
| F41 | NH-(3-Ms—Ph) |
| F42 | NHCH$_2$CO-mor |
| F43 | NHCH$_2$-(6-HO-2-Py) |
| F44 | NHCH$_2$-(6-MeO-2-Py) |
| F45 | NHCH$_2$-(6-H$_2$NOC-2-Py) |
| F46 | NHCH$_2$-(6-cyano-2-Py) |
| F47 | NHCH$_2$-(6-Me$_2$NOC-2-Py) |
| F48 | NHCH$_2$-(6-H$_2$N-2-Py) |
| F49 | NHCH$_2$-(6-Me$_2$N-2-Py) |
| F50 | NHCH$_2$-(6-F-2-Py) |
| F51 | NHCH$_2$-(6-Cl-2-Py) |
| F52 | NHCH$_2$-(6-Me-2-Py) |
| F53 | NHCH$_2$-(pyrazol-2-yl) |
| F54 | NHCH$_2$-(pyridazine-2-yl) |
| F55 | NHCH$_2$-(pyrimidine-2-yl) |
| F56 | N(CH$_2$CONH$_2$)((CH$_2$)$_2$OH) |
| F57 | NHCH(Me)CH$_2$OH |
| F58 | NHCH$_2$CH(Me)OH |

TABLE 33-continued

[Structure: benzazepine with gem-difluoro, exocyclic =CH-C(O)-R^{1A}, N-acyl with 2-CF3-4-(ethylthiomethyl... Me-CH2-S-)phenyl]

| No | R^{1A} |
|---|---|
| F59 | NHC(Me)₂CH₂OH |
| F60 | NHCH₂C(Me)₂OH |
| F61 | 3-oxo-pipa |
| F62 | NHCH₂CO-(3-H₂NOC-pipe) |
| F63 | NHCH₂CO-(4-H₂NOC-pipe) |
| F64 | NHCH(CH₂OH)₂ |

TABLE 34

[Structure: similar benzazepine with gem-difluoro, exocyclic =CH-C(O)-R^{1A}, N-acyl with 2-CF3-4-(ethylthio)phenyl]

| No | R^{1A} |
|---|---|
| G1 | NHCH₂-(2-Py) |
| G2 | NHPh |
| G3 | NHCH₂Ph |
| G4 | NHCH₂-(2-HO—Ph) |
| G5 | NHCH₂-(3-HO—Ph) |
| G6 | NHCH₂-(4-HO—Ph) |
| G7 | NHCH₂-(2-H₂NOC—Ph) |
| G8 | NHCH₂-(3-H₂NOC—Ph) |
| G9 | NHCH₂-(4-H₂NOC—Ph) |
| G10 | NH-(2-HO—Ph) |
| G11 | NH-(3-HO—Ph) |
| G12 | NH-(4-HO—Ph) |
| G13 | NH-(2-H₂NOC—Ph) |
| G14 | NH-(4-H₂NOC—Ph) |
| G15 | NH—(CH₂)₂OMe |
| G16 | NH—(CH₂)₃OH |
| G17 | N(CH₂CH₂OH)₂ |
| G18 | NHCH₂CH(CH₂OH)OH |
| G19 | N(Me)CH₂CH₂OH |
| G20 | 3-HO-pyrr |
| G21 | 3-HO-pipe |
| G22 | 4-HO-pipe |
| G23 | NHCH₂CONHMe |
| G24 | NHCH₂CONMe₂ |

TABLE 34-continued

| No | R^{1A} |
|---|---|
| G25 | N(Me)CH₂CONH₂ |
| G26 | N(Me)CH₂CONHMe |
| G27 | N(Me)CH₂CONMe₂ |
| G28 | N(CH₂CONH₂)₂ |
| G29 | NHCH(CONH₂)CH₂OH |
| G30 | 3-H₂NOC-pipe |
| G31 | 4-H₂NOC-pipe |
| G32 | NHCH₂CO-pyrr |
| G33 | NHCH₂CO-(3-HO-pyrr) |
| G34 | NHCH₂CO-(3-HO-pipe) |
| G35 | NHCH₂CO-(4-HO-pipe) |
| G36 | NH-(3-Ac—Ph) |
| G37 | NH-(3-MeHNOC—Ph) |
| G38 | NHCH₂-(4-H₂NO₂S—Ph) |
| G39 | NH-(3-Ms—Ph) |
| G40 | NHCH₂CO-mor |
| G41 | NHCH₂-(6-HO-2-Py) |
| G42 | NHCH₂-(6-MeO-2-Py) |
| G43 | NHCH₂-(6-H₂NOC-2-Py) |
| G44 | NHCH₂-(6-cyano-2-Py) |
| G45 | NHCH₂-(6-Me₂NOC-2-Py) |
| G46 | NHCH₂-(6-H₂N-2-Py) |
| G47 | NHCH₂-(6-Me₂N-2-Py) |
| G48 | NHCH₂-(6-F-2-Py) |
| G49 | NHCH₂-(6-Cl-2-Py) |
| G50 | NHCH₂-(6-Me-2-Py) |
| G51 | NHCH₂-(pyrazol-2-yl) |
| G52 | NHCH₂-(pyridazine-2-yl) |
| G53 | NHCH₂-(pyrimidine-2-yl) |
| G54 | N(CH₂CONH₂)((CH₂)₂OH) |
| G55 | NHCH(Me)CH₂OH |
| G56 | NHCH₂CH(Me)OH |
| G57 | NHC(Me)₂CH₂OH |
| G58 | NHCH₂C(Me)₂OH |
| G59 | 3-oxo-pipa |
| G60 | NHCH₂CO-(3-H₂NOC-pipe) |
| G61 | NHCH₂CO-(4-H₂NOC-pipe) |
| G62 | NHCH(CH₂OH)₂ |

TABLE 35

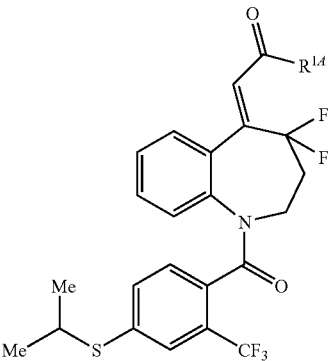

| No | R$^{1A}$ |
|---|---|
| H1 | NHCH$_2$-(2-Py) |
| H2 | NHPh |
| H3 | NHCH$_2$Ph |
| H4 | NHCH$_2$-(2-HO—Ph) |
| H5 | NHCH$_2$-(3-HO—Ph) |
| H6 | NHCH$_2$-(4-HO—Ph) |
| H7 | NHCH$_2$-(2-H$_2$NOC—Ph) |
| H8 | NHCH$_2$-(3-H$_2$NOC—Ph) |
| H9 | NHCH$_2$-(4-H$_2$NOC—Ph) |
| H10 | NH-(2-HO—Ph) |
| H11 | NH-(3-HO—Ph) |
| H12 | NH-(4-HO—Ph) |
| H13 | NH-(2-H$_2$NOC—Ph) |
| H14 | NH-(3-H$_2$NOC—Ph) |
| H15 | NH-(4-H$_2$NOC—Ph) |
| H16 | NH—(CH$_2$)$_2$OMe |
| H17 | NH—(CH$_2$)$_3$OH |
| H18 | N(CH$_2$CH$_2$OH)$_2$ |
| H19 | NHCH$_2$CH(CH$_2$OH)OH |
| H20 | N(Me)CH$_2$CH$_2$OH |
| H21 | 3-HO-pyrr |
| H22 | 3-HO-pipe |
| H23 | 4-HO-pipe |
| H24 | NHCH$_2$CONHMe |
| H25 | NHCH$_2$CONMe$_2$ |
| H26 | N(Me)CH$_2$CONH$_2$ |
| H27 | N(Me)CH$_2$CONHMe |
| H28 | N(Me)CH$_2$CONMe$_2$ |
| H29 | NH(CH$_2$)$_2$CONH$_2$ |
| H30 | N(CH$_2$CONH$_2$)$_2$ |
| H31 | NHCH(CONH$_2$)CH$_2$OH |
| H32 | 3-H$_2$NOC-pipe |
| H33 | 4-H$_2$NOC-pipe |
| H34 | NHCH$_2$CO-pyrr |
| H35 | NHCH$_2$CO-(3-HO-pyrr) |
| H36 | NHCH$_2$CO-(3-HO-pipe) |
| H37 | NHCH$_2$CO-(4-HO-pipe) |
| H38 | NH-(3-Ac—Ph) |
| H39 | NH-(3-MeHNOC—Ph) |
| H40 | NHCH$_2$-(4-H$_2$NO$_2$S—Ph) |
| H41 | NH-(3-Ms—Ph) |
| H42 | NHCH$_2$CO-mor |
| H43 | NHCH$_2$-(6-HO-2-Py) |
| H44 | NHCH$_2$-(6-MeO-2-Py) |
| H45 | NHCH$_2$-(6-H$_2$NOC-2-Py) |
| H46 | NHCH$_2$-(6-cyano-2-Py) |
| H47 | NHCH$_2$-(6-Me$_2$NOC-2-Py) |
| H48 | NHCH$_2$-(6-H$_2$N-2-Py) |
| H49 | NHCH$_2$-(6-Me$_2$N-2-Py) |
| H50 | NHCH$_2$-(6-F-2-Py) |
| H51 | NHCH$_2$-(6-Cl-2-Py) |
| H52 | NHCH$_2$-(6-Me-2-Py) |
| H53 | NHCH$_2$-(pyrazol-2-yl) |
| H54 | NHCH$_2$-(pyridazine-2-yl) |
| H55 | NHCH$_2$-(pyrimidine-2-yl) |
| H56 | N(CH$_2$CONH$_2$)((CH$_2$)$_2$OH) |
| H57 | NHCH(Me)CH$_2$OH |
| H58 | NHCH$_2$CH(Me)OH |

TABLE 35-continued

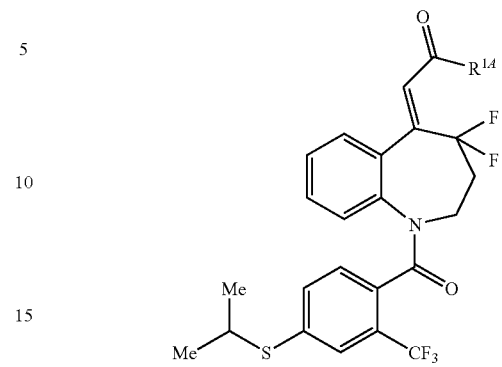

| No | R$^{1A}$ |
|---|---|
| H59 | NHC(Me)$_2$CH$_2$OH |
| H60 | NHCH$_2$C(Me)$_2$OH |
| H61 | 3-oxo-pipa |
| H62 | NHCH$_2$CO-(3-H$_2$NOC-pipe) |
| H63 | NHCH$_2$CO-(4-H$_2$NOC-pipe) |
| H64 | NHCH(CH$_2$OH)$_2$ |

TABLE 36

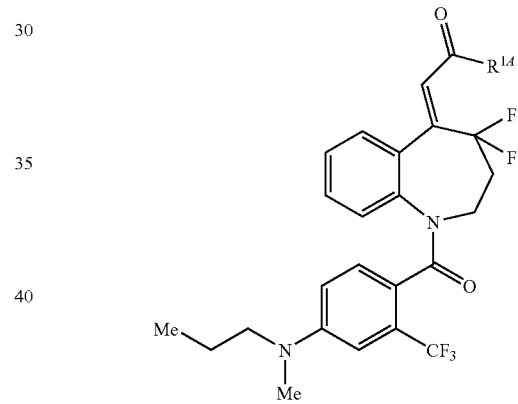

| No | R$^{1A}$ |
|---|---|
| I1 | NHCH$_2$-(2-Py) |
| I2 | NHPh |
| I3 | NHCH$_2$Ph |
| I4 | NHCH$_2$-(2-HO—Ph) |
| I5 | NHCH$_2$-(3-HO—Ph) |
| I6 | NHCH$_2$-(4-HO—Ph) |
| I7 | NHCH$_2$-(2-H$_2$NOC—Ph) |
| I8 | NHCH$_2$-(3-H$_2$NOC—Ph) |
| I9 | NHCH$_2$-(4-H$_2$NOC—Ph) |
| I10 | NH-(2-HO—Ph) |
| I11 | NH-(3-HO—Ph) |
| I12 | NH-(4-HO—Ph) |
| I13 | NH-(2-H$_2$NOC—Ph) |
| I14 | NH-(3-H$_2$NOC—Ph) |
| I15 | NH-(4-H$_2$NOC—Ph) |
| I16 | NH—(CH$_2$)$_2$OMe |
| I17 | NH—(CH$_2$)$_3$OH |
| I18 | N(CH$_2$CH$_2$OH)$_2$ |
| I19 | NHCH$_2$CH(CH$_2$OH)OH |
| I20 | N(Me)CH$_2$CH$_2$OH |
| I21 | 3-HO-pyrr |
| I22 | 3-HO-pipe |
| I23 | 4-HO-pipe |
| I24 | NHCH$_2$CONHMe |
| I25 | NHCH$_2$CONMe$_2$ |

TABLE 36-continued

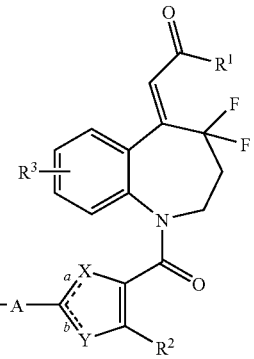

| No | R$^{14}$ |
|---|---|
| I26 | N(Me)CH$_2$CONH$_2$ |
| I27 | N(Me)CH$_2$CONHMe |
| I28 | N(Me)CH$_2$CONMe$_2$ |
| I29 | NH(CH$_2$)$_2$CONH$_2$ |
| I30 | N(CH$_2$CONH$_2$)$_2$ |
| I31 | NHCH(CONH$_2$)CH$_2$OH |
| I32 | 3-H$_2$NOC-pipe |
| I33 | 4-H$_2$NOC-pipe |
| I34 | NHCH$_2$CO-pyrr |
| I35 | NHCH$_2$CO-(3-HO-pyrr) |
| I36 | NHCH$_2$CO-(3-HO-pipe) |
| I37 | NHCH$_2$CO-(4-HO-pipe) |
| I38 | NH-(3-Ac—Ph) |
| I39 | NH-(3-MeHNOC—Ph) |
| I40 | NHCH$_2$-(4-H$_2$NO$_2$S—Ph) |
| I41 | NH-(3-Ms—Ph) |
| I42 | NHCH$_2$CO-mor |
| I43 | NHCH$_2$-(6-HO-2-Py) |
| I44 | NHCH$_2$-(6-MeO-2-Py) |
| I45 | NHCH$_2$-(6-H$_2$NOC-2-Py) |
| I46 | NHCH$_2$-(6-cyano-2-Py) |
| I47 | NHCH$_2$-(6-Me$_2$NOC-2-Py) |
| I48 | NHCH$_2$-(6-H$_2$N-2-Py) |
| I49 | NHCH$_2$-(6-Me$_2$N-2-Py) |
| I50 | NHCH$_2$-(6-F-2-Py) |
| I51 | NHCH$_2$-(6-Cl-2-Py) |
| I52 | NHCH$_2$-(6-Me-2-Py) |
| I53 | NHCH$_2$-(pyrazol-2-yl) |
| I54 | NHCH$_2$-(pyridazine-2-yl) |
| I55 | NHCH$_2$-(pyrimidine-2-yl) |
| I56 | N(CH$_2$CONH$_2$)((CH$_2$)$_2$OH) |
| I57 | NHCH(Me)CH$_2$OH |
| I58 | NHCH$_2$CH(Me)OH |
| I59 | NHC(Me)$_2$CH$_2$OH |
| I60 | NHCH$_2$C(Me)$_2$OH |
| I61 | 3-oxo-pipa |
| I62 | NHCH$_2$CO-(3-H$_2$NOC-pipe) |
| I63 | NHCH$_2$CO-(4-H$_2$NOC-pipe) |
| I64 | NHCH(CH$_2$OH)$_2$ |

The invention claimed is:

1. A method of treating nocturia, comprising administering to a patient having nocturia a pharmaceutical composition comprising a carrier and a 4,4-difluoro-1,2,3,4-tetrahydro-5H-1-benzazepine compound represented by a formula (I) or a pharmaceutically acceptable salt thereof

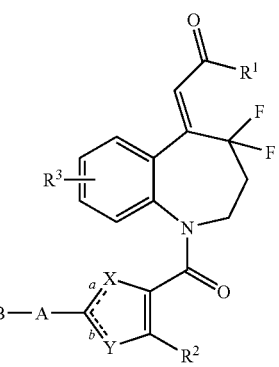

(I)

wherein the symbols have the following meanings:
R$^1$: amino which may be substituted, —OH or —O-lower alkyl,
R$^2$: CF$_3$ or halogen,
R$^3$: H or halogen,
a, b: each represents single bond or double bond, wherein one is single bond and the other is double bond,
—X—:
  (1) —CH=CH—, —CH=N—, —N=CH—, —N=N— or —S— when a is single bond and b is double bond,
  (2) —N— when a is double bond and b is single bond,
Y:
  (1) CH or N when a is single bond and b is double bond,
  (2) S when a is double bond and b is single bond,
-A-: —O—, —S—, —NH— or —N(lower alkyl), and
B: lower alkyl, lower alkenyl, lower alkynyl, cycloalkyl or aryl, each of which may be substituted.

2. A method of treating central diabetes insipidus, comprising administering to a patient having central diabetes insipidus a pharmaceutical composition comprising a carrier and a 4,4-difluoro-1,2,3,4-tetrahydro-5H-1-benzazepine compound represented by a formula (I) or a pharmaceutically acceptable salt thereof (I)

wherein the symbols have the following meanings:
R$^1$: amino which may be substituted, —OH or —O-lower alkyl,
R$^2$: CF$_3$ or halogen,
R$^3$: H or halogen,
a, b: each represents single bond or double bond, wherein one is single bond and the other is double bond, —X—:
(1) —CH=CH—, —CH=N—, —N=CH—, —N=N— or —S— when a is single bond and b is double bond,
(2) —N— when a is double bond and b is single bond, Y:
(1) CH or N when a is single bond and b is double bond,
(2) S when a is double bond and b is single bond, -A-: —O—, —S—, —NH— or —N(lower alkyl), and B: lower alkyl, lower alkenyl, lower alkynyl, cycloalkyl or aryl, each of which may be substituted.

3. The method of claim 1, wherein the composition comprises (2Z)-N-(2-hydroxyethyl)-2-{4,4,7-trifluoro-1-[4-{[(2S)-2-fluoropropyl]oxy}-2-(trifluoromethyl)benzoyl]-1,2,3,4-tetrahydro-5H-1-benzazepin-5-ylidene}acetamide or a pharmaceutically acceptable salt thereof.

4. The method of claim 1, wherein the composition comprises (2Z)-N-(2-hydroxyethyl)-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetamide or a pharmaceutically acceptable salt thereof.

5. The method of claim 1, wherein the composition comprises (2Z)-2-{4,4-difluoro-1-[4-{[(2R)-2-fluoropropyl]oxy}-2-(trifluoromethyl)benzoyl]-1,2,3,4-tetrahydro-5H-1-benzazepin-5-ylidene}-N-[(2S)-2,3-dihydroxypropyl]acetamide or a pharmaceutically acceptable salt thereof.

6. The method of claim 1, wherein the composition comprises (2Z)-N-[(2R)-2,3-dihydroxypropyl]-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetamide or a pharmaceutically acceptable salt thereof.

7. The method of claim 1, wherein the composition comprises (2Z)-2-{1-[4-(2,2-difluoropropoxy)-2-(trifluoromethyl)benzoyl]-4,4-difluoro-1,2,3,4-tetrahydro-5H-1-benzazepin-5-ylidene}-N-(2-hydroxyethyl)acetamide or a pharmaceutically acceptable salt thereof.

8. The method of claim 1, wherein the composition comprises (2Z)-2-{4,4-difluoro-1-[4-{[(2S)-2-fluoropropyl]oxy}-2-(trifluoromethyl)benzoyl]-1,2,3,4-tetrahydro-5H-1-benzazepin-5-ylidene}-N-[(2S)-2,3-dihydroxypropyl]acetamide or a pharmaceutically acceptable salt thereof.

9. The method of claim 2, wherein the composition comprises (2Z)-N-(2-hydroxyethyl)-2-{4,4,7-trifluoro-1-[4-{[(2S)-2-fluoropropyl]oxy}-2-(trifluoromethyl)benzoyl]-1,2,3,4-tetrahydro-5H-1-benzazepin-5-ylidene}acetamide or a pharmaceutically acceptable salt thereof.

10. The method of claim 2, wherein the composition comprises (2Z)-N-(2-hydroxyethyl)-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetamide or a pharmaceutically acceptable salt thereof.

11. The method of claim 2, wherein the composition comprises (2Z)-2-{4,4-difluoro-1-[4-{[(2R)-2-fluoropropyl]oxy}-2-(trifluoromethyl)benzoyl]-1,2,3,4-tetrahydro-5H-1-benzazepin-5-ylidene}-N-[(2S)-2,3-dihydroxypropyl]acetamide or a pharmaceutically acceptable salt thereof.

12. The method of claim 2, wherein the composition comprises (2Z)-N-[(2R)-2,3-dihydroxypropyl]-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetamide or a pharmaceutically acceptable salt thereof.

13. The method of claim 2, wherein the composition comprises (2Z)-2-{1-[4-(2,2-difluoropropoxy)-2-(trifluoromethyl)benzoyl]-4,4-difluoro-1,2,3,4-tetrahydro-5H-1-benzazepin-5-ylidene}-N-(2-hydroxyethyl)acetamide or a pharmaceutically acceptable salt thereof.

14. The method of claim 2, wherein the composition comprises (2Z)-2-{4,4-difluoro-1-[4-{[(2S)-2-fluoropropyl]oxy}-2-(trifluoromethyl)benzoyl]-1,2,3,4-tetrahydro-5H-1-benzazepin-5-ylidene}-N-[(2S)-2,3-dihydroxypropyl]acetamide or a pharmaceutically acceptable salt thereof.

15. A method of treating urinary incontinence or nocturnal enuresis comprising administering to a patient having urinary incontinence or nocturnal enuresis a pharmaceutical composition comprising a carrier and a 4,4-difluoro-1,2,3,4-tetrahydro-5H-1-benzazepine compound represented by a formula (I) or a pharmaceutically acceptable salt thereof

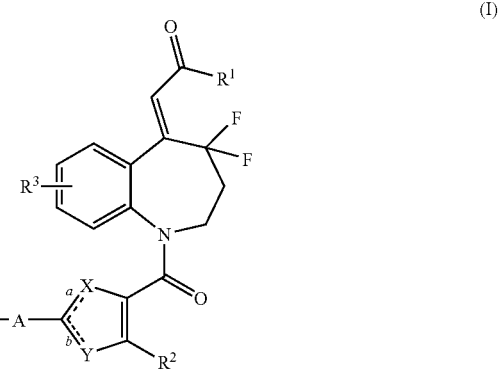

(I)

wherein the symbols have the following meanings:

$R^1$: amino which may be substituted, —OH or —O-lower alkyl, $R^2$: $CF_3$ or halogen, $R^3$: H or halogen, a, b: each represents single bond or double bond, wherein one is single bond and the other is double bond, —X—:
(1) —CH=CH—, —CH=N—, —N=CH—, —N=N— or —S— when a is single bond and b is double bond,
(2) —N— when a is double bond and b is single bond, Y:
(1) CH or N when a is single bond and b is double bond,
(2) S when a is double bond and b is single bond, -A-: —O—, —S—, —NH— or —N(lower alkyl), and B: lower alkyl, lower alkenyl, lower alkynyl, cycloalkyl or aryl, each of which may be substituted.

16. The method of claim 15, which is a method of treating nocturnal enuresis.

17. The method of claim 16, wherein the composition comprises (2Z)-N-(2-hydroxyethyl)-2-{4,4,7-trifluoro-1-[4-{[(2S)-2-fluoropropyl]oxy}-2-(trifluoromethyl)benzoyl]-1,2,3,4-tetrahydro-5H-1-benzazepin-5-ylidene}acetamide or a pharmaceutically acceptable salt thereof.

18. The method of claim 16, wherein the composition comprises (2Z)-N-(2-hydroxyethyl)-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetamide or a pharmaceutically acceptable salt thereof.

19. The method of claim 16, wherein the composition comprises (2Z)-2-{4,4-difluoro-1-[4-{[(2R)-2-fluoropropyl]oxy}-2-(trifluoromethyl)benzoyl]-1,2,3,4-tetrahydro-5H-1-benzazepin-5-ylidene}-N-[(2S)-2,3-dihydroxypropyl]acetamide or a pharmaceutically acceptable salt thereof.

20. The method of claim 16, wherein the composition comprises (2Z)-N-[(2R)-2,3-dihydroxypropyl]-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetamide or a pharmaceutically acceptable salt thereof.

21. The method of claim 16, wherein the composition comprises (2Z)-2-{1-[4-(2,2-difluoropropoxy)-2-(trifluoromethyl)benzoyl]-4,4-difluoro-1,2,3,4-tetrahydro-5H-1-benzazepin-5-ylidene}-N-(2-hydroxyethyl)acetamide or a pharmaceutically acceptable salt thereof.

22. The method of claim 16, wherein the composition comprises (2Z)-2-{4,4-difluoro-1-[4-{[(2S)-2-fluoropropyl]oxy}-2-(trifluoromethyl)benzoyl]-1,2,3,4-tetrahydro-5H-1-benzazepin-5-ylidene}-N-[(2S)-2,3-dihydroxypropyl]acetamide or a pharmaceutically acceptable salt thereof.

* * * * *

UNITED STATES PATENT AND TRADEMARK OFFICE
CERTIFICATE OF CORRECTION

PATENT NO. : 7,807,664 B2
APPLICATION NO. : 11/598732
DATED : October 5, 2010
INVENTOR(S) : Hiroyuki Koshio et al.

Page 1 of 1

It is certified that error appears in the above-identified patent and that said Letters Patent is hereby corrected as shown below:

Title page, item (73) Assignee, "Astella" should read --Astellas--.

Signed and Sealed this
Fourth Day of January, 2011

David J. Kappos
*Director of the United States Patent and Trademark Office*